United States Patent [19]

Gopalan

[11] Patent Number: 5,302,720
[45] Date of Patent: Apr. 12, 1994

[54] BIPHENYL-SUBSTITUTED GUANIDINE DERIVATIVES USEFUL AS HYPOGLYCAEMIC AGENTS

[75] Inventor: Balasubramanian Gopalan, Bombay, India

[73] Assignee: The Boots Company, England

[21] Appl. No.: 899,939

[22] Filed: Jun. 17, 1992

Related U.S. Application Data

[63] Continuation of Ser. No. 701,695, May 16, 1991, abandoned.

[30] Foreign Application Priority Data

Jun. 28, 1990 [GB] United Kingdom ............... 9014456

[51] Int. Cl.$^5$ ............... C07D 211/46; A61K 31/445
[52] U.S. Cl. ............... 546/216; 544/56; 544/165; 544/330; 544/402; 544/58.2; 544/383; 544/398; 546/225; 546/231; 546/223; 546/332; 548/300.1; 548/369; 548/326.5; 548/541; 564/238; 564/245; 564/239
[58] Field of Search ............... 514/327, 227.5, 238.5, 514/255, 330, 329, 331, 357, 424, 392, 634; 544/59, 165, 330, 402, 58.2, 383, 398; 546/216, 231, 223, 332, 225; 548/315, 569, 326.5, 541; 564/238, 245, 239

[56] References Cited

U.S. PATENT DOCUMENTS

| | | | |
|---|---|---|---|
| 1,850,682 | 3/1932 | Meis | 546/231 |
| 3,252,982 | 5/1966 | Mizzoni et al. | 546/231 |
| 3,300,494 | 1/1967 | Cragoe | 260/250 |
| 3,669,974 | 6/1972 | Elpern et al. | 544/398 |
| 3,783,162 | 1/1974 | Grisar et al. | 514/329 |
| 4,013,716 | 3/1977 | Abblard et al. | 260/553 A |
| 4,061,746 | 12/1977 | Blohm et al. | 424/244 |
| 4,101,659 | 7/1978 | Rasmussen | 514/331 |
| 4,169,852 | 10/1979 | Landauer | 260/564 RF |
| 4,281,004 | 7/1981 | Ives | 546/332 |
| 4,414,211 | 11/1983 | Rasmussen | 544/165 |
| 4,680,300 | 7/1987 | Nelson et al. | 514/312 |
| 4,693,850 | 9/1987 | Maryanoff et al. | 260/506 |
| 4,709,094 | 11/1987 | Weber et al. | 564/238 |
| 4,781,866 | 11/1988 | Maryanoff et al. | 260/506 |
| 5,223,498 | 6/1993 | Gopalan | 514/231.2 |

FOREIGN PATENT DOCUMENTS 017484 10/1980 European Pat. Off. .

(List continued on next page.)

OTHER PUBLICATIONS

Leffek et al., K. T.: Basicity of substituted 2--phenyl-1,1,3,3-tetramethylguanidines and other bases in acetonitrile solvent. *Can J. Chem.*, vol. 67, pp. 590–595 (1989).

(List continued on next page.)

*Primary Examiner*—Jose G. Dees
*Assistant Examiner*—B. Frazier
*Attorney, Agent, or Firm*—Ostrolenk, Faber, Gerb & Soffen

[57] ABSTRACT

Compounds of formula I

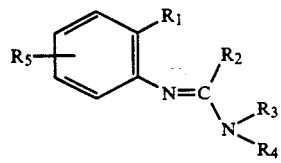

and their salts in which $R_1$ is optionally substituted phenyl, $R_2$ is alkyl, cycloalkyl or optionally substituted amino, or $R_2$ and $R_3$ together with the nitrogen and carbon atoms to which they are attached form an optionally substituted heterocyclic ring or $R_3$ and $R_4$ together with the nitrogen atom to which they are attached form an optionally substituted heterocyclic ring and $R_5$ is H, halo, alkyl, alkoxy, trifluoromethyl or a group of formula $S(O)_m R_8$ in which m is 0, 1 or 2 and $R_8$ is alkyl have utility in the treatment of diabetes particularly in the treatment of hyperglycaemia.

33 Claims, No Drawings

FOREIGN PATENT DOCUMENTS

| | | |
|---|---|---|
| 024779 | 3/1981 | European Pat. Off. . |
| 073971 | 3/1983 | European Pat. Off. . |
| 144892 | 6/1985 | European Pat. Off. . |
| 233461 | 1/1986 | European Pat. Off. . |
| 195620 | 9/1986 | European Pat. Off. . |
| 0195620 | 9/1986 | European Pat. Off. . |
| 3108564 | 11/1982 | Fed. Rep. of Germany ...... 564/238 |
| 3220828 | 12/1983 | Fed. Rep. of Germany . |
| 158084 | 9/1986 | India . |
| 614072 | 12/1948 | United Kingdom . |
| 2038305 | 7/1980 | United Kingdom . |

OTHER PUBLICATIONS

Cymerman J. and Short W. F.: Amidines Part XII. Preparation of 9-Substituted Phenanthridines from N-2-Diphenylylamidines. *J Chem Soc* (1949) pp. 703-707.

Charlton et al, P. T.:Antituberculous Compounds Part VII. Some Further N-Substituted Amidines and Analogues. *J Chem Soc* (1951) pp. 485-492.

Pruszynski P. Synthesis and properties of phenyl substituted derivatives of 2-phenyl-1,1,3,3-tetramethylguanidine. *Can J Chem* 65 (1987) pp. 626-629.

Chemical Abstracts 90 137822x (1979).

Chemical Abstracts 107 59051y (1987).

Derwent Abstract 79-02894B (1979).

Derwent Abstract 85-091832/15 (1985).

Derwent Abstract 91204X/49 (1991).

BIPHENYL-SUBSTITUTED GUANIDINE DERIVATIVES USEFUL AS HYPOGLYCAEMIC AGENTS

This is a continuation of application Ser. No. 07/701,695 filed on May 16, 1991, now abandoned.

This invention relates to novel therapeutic agents useful as antidiabetic agents, particularly as hypoglycaemic agents, to processes for the preparation of such agents and to pharmaceutical compositions containing them.

The present invention provides compounds of formula I:

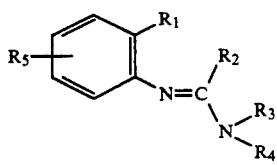

and their pharmaceutically acceptable salts, in which $R_1$ is phenyl optionally substituted by halo, alkyl of 1 to 3 carbon atoms, alkoxy of 1 to 3 carbon atoms, alkanoyl of 2 to 4 carbon atoms, or a group of formula $S(O)_nR_8$ in which $n=0$ or 1 and $R_8$ is an alkyl group of 1 to 3 carbon atoms;

$R_2$ is a straight or branched alkyl group containing 1 to 4 carbon atoms, a cycloalkyl group containing 3 to 7 carbon atoms or a group of formula II

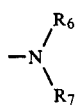

in which $R_6$ and $R_7$, which are the same or different, are H or an alkyl group containing 1 to 4 carbon atoms;

$R_3$ is H or a straight or branched aliphatic group of 1 to 4 carbon atoms;

$R_4$ is (a) H, (b) a straight or branched aliphatic group of 1 to 6 carbon atoms optionally substituted by hydroxy or an acylated derivative thereof, by an alkoxy group containing 1 to 3 carbon atoms, by an alkylthio group containing 1 to 3 carbon atoms, by an optionally alkylated amino group, by a carbocyclic group containing 3 to 7 carbon atoms, by pyridyl or by cyano, (c) a carbocyclic ring containing 3 to 7 carbon atoms and optionally substituted by hydroxy with the proviso that $R_3$, $R_4$, $R_6$ are $R_7$ are not all methyl when $R_1$ is phenyl; or the group $R_2$ and the group $R_3$ together with the carbon and nitrogen atoms to which they are attached form a heterocyclic ring of formula III

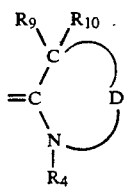

in which $R_4$, $R_9$ and $R_{10}$, which are the same or different, are H or an alkyl group of 1 to 4 carbon atoms and D is an alkylene group of 2 to 5 carbon atoms optionally substituted by one or more alkyl groups of 1 to 3 carbon atoms; or the group $R_2$ and the group $R_3$ together with the carbon and nitrogen atoms to which they are attached form a heterocyclic ring of formula IV

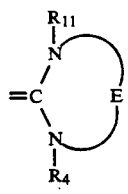

in which $R_4$ is as hereinbefore described except that $R_4$ cannot be H, in which $R_{11}$ is H or an alkyl group containing 1 or 2 carbon atoms, and E is an alkylene group of 2 to 4 carbon atoms optionally substituted by one or more alkyl groups containing 1 to 3 carbon atoms; or $R_3$ and $R_4$ together with the nitrogen atom to which they are attached form a heterocyclic ring of formula V

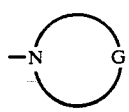

in which

G is an alkylene group of 4 to 6 carbon atoms optionally interrupted by oxygen, sulphur, sulphinyl, sulphonyl, or nitrogen optionally substituted by (a) a carbocyclic ring containing 3 to 7 carbon atoms (b) a methylsulphonyl group or (c) an alkyl group containing 1 to 3 carbon atoms and optionally substituted by hydroxy or an alkoxy group containing 1 to 3 carbon atoms, said alkylene group being optionally substituted by (a) one or more alkyl groups containing 1 to 3 carbon atoms and optionally substituted by hydroxy, (b) by one or more hydroxy groups or an ester thereof, (c) by one or more alkoxy groups, (d) by oxo or a derivative thereof (e.g. an oxime or oxime ether) or (e) by one or more groups of formula $S(O)_mR_8$ in which $m=0$ or 1 and $R_8$ is an alkyl group containing 1 to 3 carbon atoms and $R_5$ represents H or one or more optional substituents selected from halo, alkyl groups containing 1 to 4 carbon atoms, alkoxy groups containing 1 to 3 carbon atoms, trifluoromethyl, or groups of formula $S(O)_mR_8$ in which m is 0,1 or 2 and $R_8$ is an alkyl group containing 1 to 3 carbon atoms.

In preferred compounds of formula I, $R_1$ is phenyl, 2-fluorophenyl, 3-fluorophenyl, 4-fluorophenyl, 4-chlorophenyl, 4-methoxyphenyl, 3-methylphenyl, 4-methylphenyl, 3-methylthiophenyl, 3-methanesulphonylphenyl, 4-methanesulphonylphenyl or 4-acetylphenyl.

In preferred compounds in which $R_2$ is an alkyl group, the group $R_2$ contains 1 to 5 carbon atoms (eg t-butyl). In preferred compounds of formula I in which the group $R_2$ is a cycloalkyl group, the cycloalkyl group is cyclohexyl.

In preferred compounds of formula I in which R$_2$ is a group of formula II, R$_6$ and R$_7$ are independently H or methyl (for example R$_2$ is amino or methylamino).

In preferred compounds of formula I in which the group R$_3$ and R$_4$ do not form part of a heterocyclic ring, the group R$_3$ is H or an alkyl group containing 1 to 3 carbon atoms (eg methyl or ethyl) and the group R$_4$ is (a) H, (b) an alkyl group of 1 to 3 carbon atoms (e.g. ethyl) optionally substituted by methoxy, pyridyl or dimethylamino (e.g. R$_4$ is 2-methoxyethyl, 2-pyridylethyl or 2-dimethylaminoethyl) or (c) a phenyl group substituted by hydroxy.

In one group of preferred compounds of formula I in which the groups R$_2$ and R$_3$ together with the carbon and nitrogen atoms to which they are attached form a heterocyclic ring of formula III, R$_9$ and R$_{10}$, which may be the same or different, are H or alkyl groups containing 1 to 3 carbon atoms (for example methyl), D is —(CH$_2$)$_3$— and the group R$_4$ is H. In particularly preferred compounds, formula III represents 2-piperidinylidene.

In a second group of preferred compounds of formula I in which the groups R$_2$ and R$_3$ together with the carbon and nitrogen atoms to which they are attached form a heterocyclic ring of formula IV, E is —CH$_2$CH$_2$—, R$_{11}$ is H or methyl and R$_4$ is methyl, n-butyl or 2-hydroxyethyl. In particularly preferred compounds, formula IV represents 1-methyl-2-imidazolidinylidene, 1-(n-butyl)-2-imidazolidinylidene, 1-(2-hydroxyethyl)-2-imidazolidinylidene or 1,3-dimethyl-2-imidazolidinylidene.

In preferred compounds of formula I in which R$_3$ and R$_4$ together with the nitrogen atom to which they are attached form a heterocyclic ring of formula V, G represents a group selected from
—(CH$_2$)$_4$—,
—(CH$_2$)$_5$—,
—CH$_2$—CH=CH—(CH$_2$)$_2$—,
—(CH$_2$)$_2$O(CH$_2$)$_2$—,
—(CH$_2$)$_2$OCHMeCH$_2$—
—CMe$_2$CH$_2$O(CH$_2$)$_2$—
—(CH$_2$)$_2$S(CH$_2$)$_2$—,
—(CH$_2$)$_2$SO(CH$_2$)$_2$—,
—(CH$_2$)$_2$SO$_2$(CH$_2$)$_2$—,
—(CH$_2$)$_2$NMe(CH$_2$)$_2$—,
—(CH$_2$)$_2$NEt(CH$_2$)$_2$—
—(CH$_2$)$_2$N(SO$_2$Me)(CH$_2$)$_2$—,
—(CH$_2$)$_2$N(CH$_2$CH$_2$OH)(CH$_2$)$_2$—,
—(CH$_2$)$_2$CHMe(CH$_2$)$_2$—,
—CH$_2$CH(OH)(CH$_2$)$_2$—,
—CH$_2$CH(OH)(CH$_2$)$_3$—,
—CH$_2$CH(CH OH)(CH$_2$)$_3$—,
—(CH$_2$)$_2$CH(CH$_2$OH)(CH$_2$)$_2$—,
—(CH$_2$)$_2$CH(OH)(CH$_2$)$_2$—,
—(CH$_2$)$_2$C(OH)(Me)(CH$_2$)$_2$—,
—(CH$_2$)$_2$CH(OMe)(CH$_2$)$_2$—,
—CH$_2$CH(OMe)(CH$_2$)$_3$—,
—(CH$_2$)$_2$CH(CONMe$_2$)(CH$_2$)$_2$—
—(CH$_2$)$_2$CO(CH$_2$)$_2$—
—(CH$_2$)$_2$C=NOH(CH$_2$)$_2$—,
—(CH$_2$)$_2$C=NOMe(CH$_2$)$_2$—.

In particularly preferred compounds of formula I in which R$_3$ and R$_4$ together form a heterocyclic ring of formula V, the group NR$_3$R$_4$ is 3-hydroxy-1-pyrrolidinyl, piperidino, 1,2,5,6-tetrahydropyridyl, 4-methylpiperidino, 3-hydroxypiperidino, 4-hydroxypiperidino, 4-hydroxy-4-methylpiperidino, 3-methoxypiperidino, 4-methoxypiperidino, 3-hydroxymethylpiperidino, 4-hydroxymethylpiperidino, 4-dimethylcarbamoylpiperidino, 4-piperidinon-1-yl, 4-piperidinon-1-yl oxime, 4-piperidinon-1-yl oxime-O-methyl ether, morpholino, 2-methylmorpholino, 3,3-dimethylmorpholino, thiomorpholino, thiomorpholino-1-oxide, thiomorpholino-1,1-dioxide, 4-methyl-1-piperazinyl, 4-ethyl-1-piperazinyl, 4-(2-hydroxyethyl)-1-piperazinyl, 4-methyl-sulphonyl-1-piperazinyl.

In particularly preferred compounds of formula I the group is —N=C(R$_2$)NR$_3$R$_4$ is
N-methylpivalamidino,
cyclohexanecarboxamidino,
N,N-dimethylguanidino,
N,N'-dimethylguanidino,
N-methyl-N-(2-pyridylethyl)guanidino,
N-ethyl-N-(2-methoxyethyl)guanidino,
N-methyl-N-(2-dimethylaminoethyl)guanidino,
N-(4-hydroxyphenyl)-N-methylguanidino,
N,N-(3-oxapentamethylene)guanidino,
N,N-(2-methyl-3-oxapentamethylene)guanidino,
N,N-(1,1-dimethyl-3-oxapentamethylene)guanidino,
N,N-(3-thiapentamethylene)guanidino,
N,N-(3-thiapentamethylene)guanidino S-oxide,
N,N-(3-thiapentamethylene)guanidino S,S-dioxide,
N,N-(3-methyl-3-azapentamethylene)guanidino,
N,N-(3-ethyl-3-azapentamethylene)guanidino,
N,N-[3-(2-hydroxyethyl)-3-azapentamethylene]-guanidino,
N,N-(3-methylsulphonyl-3-azapentamethylene)-guanidino,
N,N-(2-hydroxytetramethylene)guanidino,
N,N-pentamethyleneguanidino,
N,N-(2-pentenylene)guanidino,
N,N-(3-methylpentamethylene)guanidino,
N,N-(2-hydroxypentamethylene)guanidino,
N,N-(3-hydroxypentamethylene)guanidino,
N,N-(3-hydroxy-3-methylpentamethylene)guanidino,
N,N-(2-hydroxymethylpentamethylene)guanidino,
N,N-(3-hydroxymethylpentamethylene)guanidino,
N,N-(3-dimethylcarbamoylpentamethylene)guanidino,
N,N-(2-methoxypentamethylene)guanidino,
N,N-(3-methoxypentamethylene)guanidino,
N,N-(3-oxopentamethylene)guanidino
N,N-(3-hydroxyiminopentamethylene)guanidino
N,N-(3-methoxyiminopentamethylene)guanidino.

In preferred compounds of formula I, R$_5$ represents H or one or more substituents (preferably one or two substituents) selected from fluoro, methyl, methoxy, or methylthio. Where more than one substituent is present they may be the same or different.

Specific compounds of formula I are:
2-(2-piperidinylideneamino)biphenyl
2-(1,3-dimethyl-2-imidazolidinylideneamino)-biphenyl
N-(2-biphenylyl)-N'-methylpivalamidine
N-(2-biphenylyl)cyclohexane-1-carboxamidine
2-(1-methyl-2-imidazolidinylideneamino)biphenyl
2-(1-n-butyl-2-imidazolidinylideneamino)biphenyl
2-[1-(2-hydroxyethyl)-2-imidazolidinylideneamino]-biphenyl
N-(2-biphenylyl)-N',N''-dimethylguanidine
N-(2-biphenylyl)-N',N'-dimethylguanidine
N-(4-methoxy-2-biphenylyl)-N',N'-dimethylguanidine
N-(2-biphenylyl)morpholine-4-carboxamidine
N-(4-methoxy-2-biphenylyl)morpholine-4-carboxamidine
N-(5-methoxy-2-biphenylyl)piperidine-1-carboxamidine
N-(3'-methyl-2-biphenylyl)piperidine-1-carboxamidine N-(4'-methanesulphonyl-2-biphenylyl)piperidine-1-carboxamidine
N-(4-methyl-2-biphenylyl)morpholine-4-carboxamidine
N-(5-methoxy-2-biphenylyl)-N',N'-dimethylguanidine
N,N-dimethyl-N'-(5-methylthio-2-biphenylyl)-guanidine
N-(4'-acetyl-2-biphenylyl)-N',N'-dimethylguanidine
N,N-dimethyl-N'-(3-methyl-2-biphenylyl)-guanidine
N,N-dimethyl-N'-(6-methyl-2-biphenylyl)-guanidine
N-(5-fluoro-2-biphenylyl)-N',N'-dimethylguanidine
N-(3'-fluoro-2-biphenylyl)-N',N'-dimethylguanidine
N,N-dimethyl-N'-(3'-methyl-2-biphenylyl)guanidine
N,N-dimethyl-N'-(4'-methanesulphonyl-2-biphenyl)-guanidine
N,N-dimethyl-N'-(4'-methyl-2-biphenylyl)guanidine
N-(2-biphenylyl)-N'-(4-hydroxyphenyl)-N'-methylguanidine
N,N-dimethyl-N'-(3'-methylthio-2-biphenyl)guanidine
N-(2-biphenylyl)piperidine-1-carboxamidine
N-(2-biphenylyl)-1,2,5,6-tetrahydropyridine-1-carboxamidine
N-(2-biphenylyl)-4-methylpiperidine-1-carboxamidine
N-(2-biphenylyl)-4-hydroxypiperidine-1-carboxamidine
N-(4-fluoro-2-biphenylyl)-4-hydroxypiperidine-1-carboxamidine
N-(5-fluoro-2-biphenylyl)-4-hydroxypiperidine-1-carboxamidine
N-(3-methyl-2-biphenylyl)-4-hydroxypiperidine-1-carboxamidine
N-(5-methyl-2-biphenylyl)-4-hydroxypiperidine-1-carboxamidine
N-(4-methylthio-2-biphenylyl)-4-hydroxypiperidine-1-carboxamidine
N-(5-methylthio-2-biphenylyl)-4-hydroxypiperidine-1-carboxamidine
N-(2-biphenylyl)-4-methoxypiperidine-1-carboxamidine
N-(2-biphenylyl)-3-methoxypiperidine-1-carboxamidine
N-(2-biphenylyl)-3-hydroxymethylpiperidine-1-carboxamidine
N-(2-biphenylyl)-4-hydroxymethylpiperidine-1-carboxamidine
N-(2-biphenylyl)-4-methoxyiminopiperidine-1-carboxamidine
N-(2-biphenylyl)-4-hydroxy-4-methylpiperidine-1-carboxamidine
N-(2-biphenylyl)-4-dimethylcarbamoylpiperidine-1-carboxamidine
N-(5-methylthio-2-biphenylyl)morpholine-4-carboxamidine
N-(2-biphenylyl)-2-methylmorpholine-4-carboxamidine
N-(2-biphenylyl)-3,3-dimethylmorpholine-4-carboxamidine
N-(2-biphenylyl)thiomorpholine-4-carboxamidine
N-(2-biphenylyl)thiomorpholine-1,1-dioxide-4-carboxamidine
N-(2-biphenylyl)-3-hydroxypyrrolidine-1-carboxamidine
N-(2-biphenylyl)-4-methylpiperazine-1-carboxamidine
N-(4-fluoro-2-biphenylyl)-4-methylpiperazine-1-carboxamidine
N-(5-fluoro-2-biphenylyl)-4-methylpiperazine-1-carboxamidine
N-(3-methyl-2-biphenylyl)-4-methylpiperazine-1-carboxamidine
N-(5-methyl-2-biphenylyl)-4-methylpiperazine-1-carboxamidine
N-(4-methylthio-2-biphenylyl)-4-methylpiperazine-1-carboxamidine
N-(5-methylthio-2-biphenylyl)-4-methylpiperazine-1-carboxamidine
N-(2-biphenylyl)-4-ethylpiperazine-1-carboxamidine
N-(2-biphenylyl)-4-(2-hydroxyethyl)piperazine-1-carboxamidine
N-(2-biphenylyl)-N'-methyl-N'-[2-(2-pyridyl)-ethyl]-guanidine
N-(2-biphenylyl)-N'-ethyl-N'-(2-methoxyethyl)-guanidine
N-(2-biphenylyl)-N'-methyl-N'-(2-dimethylaminoethyl)guanidine
N-(2-biphenylyl)-4-methanesulphonylpiperazine-1-carboxamidine
N-(2-biphenylyl)-4-piperidone-1-carboxamidine
N-(3'-methanesulphonyl-2-biphenylyl)-N',N'-dimethylguanidine
N-(4'-chloro-2-biphenylyl)-N',N'-dimethylguanidine
N-(4'-fluoro-2-biphenylyl)-4-hydroxypiperidine-1-carboxamidine
N-(2'-fluoro-2-biphenylyl)-4-methylpiperazine-1-carboxamidine
N-(2'-fluoro-2-biphenylyl)-4-hydroxypiperidine-1-carboxamidine
N-(3'-fluoro-2-biphenylyl)-4-hydroxypiperidine-1-carboxamidine
N-(3'-fluoro-2-biphenylyl)-4-methylpiperazine-1-carboxamidine
N-(2-biphenylyl)-3-hydroxypiperidine-1-carboxamidine
N-(2-biphenylyl)-4-hydroxyiminopiperidine-1-carboxamidine
N-(2-biphenylyl)thiomorpholine-1-oxide-4-carboxamidine
N-(4'-methoxy-2-biphenylyl)-N',N'-dimethylguanidine
and pharmaceutically acceptable salts thereof.

Compounds of formula I may exist as salts with pharmaceutically acceptable acids. Examples of such salts include hydrochlorides, hydrobromides, hydriodides, sulphates, nitrates, maleates, acetates, citrates, fumarates, tartrates, succinates, benzoates, pamoates and salts with acidic amino acids such as glutamic acid. Compounds of formula I and their salts may exist in the form of solvates (for example hydrates).

Some compounds of formula I contain one or more asymmetric carbon atoms and exist in different optically active forms. When the compounds of formula I contain one chiral centre the compounds exist in two enantiomeric forms and the present invention includes both enantiomeric forms and mixtures thereof. When the compounds of formula I contain more than one chiral centre, the compounds may exist in diastereoisomeric forms. The present invention includes each of these diastereoisomeric forms and mixtures thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 50 to 500 mg of the active compound. Other compositions for oral administration include, for example, aqueous solutions containing the active compound, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat hyperglycaemia in human beings. In such treatment the amount of the compound of formula I administered per day is in the range 50 to 3000 mg. The preferred administration route is oral administration.

Processes for the preparation of compounds of formula I will now be described. These processes form a further aspect of the present invention.

Compounds of formula I may be prepared by the reaction of an aminophenyl compound of formula VI

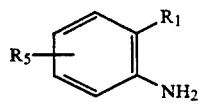
VI with an amide or a urea of formula $R_2.CO.NR_3R_4$ in the presence of a condensing agent such as phosphorus oxychloride, thionyl chloride, phosgene, phosphorus pentachloride or benzenesulphonyl chloride.

Compounds of formula I in which the groups $R_2$ and $R_3$ together with the carbon and nitrogen atoms to which they are attached form a ring represented by formula III may be prepared by the reaction of an aminophenyl compound of formula VI with a) a lactam of formula VII

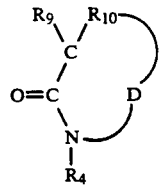
VII in the presence of a condensing agent such as phosphorus oxychloride, thionyl chloride, cyanuric chloride, phosgene, carbon tetrachloride/triphenylphosphine, phosphorus pentachloride or benzenesulphonyl chloride.

b) a compound of formula VIII

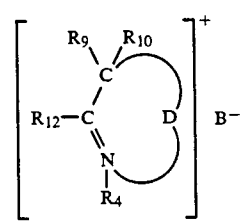
VIII in which $R_{12}$ is chloro, $-O-POCl_2$, $-O-SOCl$, $-O-COCl$ or $-OSO_2Ph$ and $B^-$ is an anion such as halo (e.g. $Cl^-$) or $POCl_4$.

c) a compound of formula IX

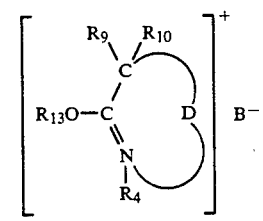
IX in which $R_{13}$ is an alkyl group and $B^-$ is an anion such as fluoroborate or methosulphate.

d) when $R_4$ is H, a ketoxime of formula X

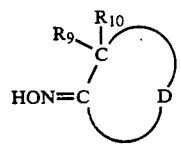
X in the presence of a sulphonyl chloride (for example benzene sulphonyl chloride).

Compounds of formula I in which the groups $R_2$ and $R_3$ together with the carbon and nitrogen atoms to which they are attached form a ring represented by formula IV may be prepared by the reaction of an aminophenyl compound of formula VI with a urea of formula XI

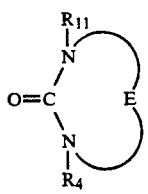

XI in the presence of a condensing agent such as phosphorus oxychloride, thionyl chloride, phosgene, phosphorus pentachloride or benzenesulphonyl chloride.

Compounds of formula I in which the groups $R_2$ and $R_3$ together with the carbon and nitrogen atoms to which they are attached form a ring represented by formula IV may be prepared by the reaction of a compound of formula XII

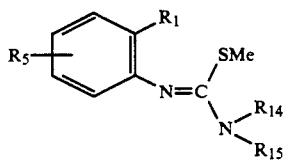

XII optionally in the form of a salt (e.g. a hydriodide salt) in which $R_{14}$ and $R_{15}$ are H with a diamine of formula XIII

 R$_{11}$NHENHR$_4$   XIII

Compounds of formula I in which $R_2$ is a straight or branched alkyl group of 1 to 4 carbon atoms or a cycloalkyl group of 3 to 7 carbon atoms and the group $NR_3R_4$ is $NH_2$ may be prepared by the reaction of a compound of formula VI optionally in the form of a salt (e.g. a hydrochloride salt) with a cyano compound of formula $R_2CN$, optionally in the presence of aluminium chloride.

Compounds of formula I in which the group $R_2$ is $NH_2$ may be prepared by the reaction of a compound of formula VI optionally in the form of a salt (e.g. a hydrochloride salt) with a cyanamide compound of formula $R_3R_4NCN$. The reaction may be performed in a liquid reaction medium (for example m-cresol) or by heating the reactants together in the absence of a liquid carrier.

Compounds of formula I in which the group $R_2$ is $NH_2$ may be prepared by the reaction of compounds of formula XIV

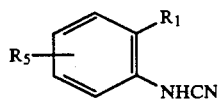

XIV with the amines of formula $NHR_3R_4$ optionally in a liquid reaction medium (for example ethanol).

Compounds of formula I in which $R_2$ is a group of formula II in which $R_6$ is alkyl and $R_7$ is H or alkyl may be prepared by the reaction of a compound of formula XII in which $R_{14}$ is the group $R_6$ and $R_{15}$ is the group $R_7$ with an amine of formula $HNR_3R_4$. The reaction may be performed in an alcoholic medium (e.g. ethanol or n-butanol) optionally in the presence of a base such as pyridine or triethylamine or in the presence of potassium hydroxide and lead acetate. When $HNR_3R_4$ is ammonia, the ammonia may be dissolved in the alcoholic medium and the reaction may be performed under elevated pressure in a sealed reaction vessel.

Compounds of formula I in which $R_2$ is a group of formula II in which $R_6$ is alkyl and $R_7$ is H or alkyl may be prepared by the reaction of a thiourea of formula XV

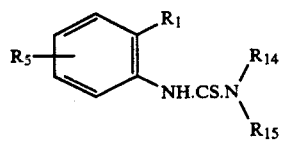

XV in which $R_{14}$ is the group $R_6$ and $R_{15}$ is the group $R_7$ with an amine of formula $HNR_3R_4$. The reaction may be performed in the presence of a base (such as potassium hydroxide or potassium carbonate) and lead acetate. When $HNR_3R_4$ is ammonia, the ammonia may be dissolved in an alcoholic medium (e.g. ethanol) and the reaction may be performed under elevated pressure in a sealed reaction vessel.

Compounds of formula I in which $R_2$ is a group of formula II in which $R_6$ is alkyl and $R_7$ is H and in which $R_3$ is H may be prepared by the reaction of a carbodiimide of formula XVI

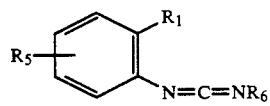

XVI with an amine of formula $H_2NR_4$.

Compounds of formula VI may be prepared by the reduction of the nitro group in a compound of formula XVII

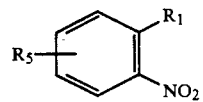

XVII for example (a) using hydrogen and a Raney nickel catalyst, (b) hydrogen and a palladium/carbon catalyst, (c) sodium sulphide, (d) stannous chloride dihydrate in hydrochloric acid, ethyl acetate or ethanol or (e) iron in the presence of acid.

Compounds of formula VIII in which $R_{12}$ is a group of formula $OPOCl_2$, $OSOCl$, $OCOCl$ and $OSO_2Ph$ may be prepared by the reaction of compounds of formula VII with phosphorus oxychloride, thionyl chloride, phosgene or benzenesulphonyl chloride respectively.

Compounds of formula IX may be prepared by the reaction of compounds of formula VII with alkylating agents such as dialkylsulphate, trialkyloxonium fluoroborate or borontrifluoride etherate/diazoalkanes followed by basification with sodium carbonate or sodium hydroxide solution.

Compounds of formula XII may be prepared by the reaction of methyl iodide with thioureas of formula XV.

Compounds of formula XIV may be prepared by the reaction of potassium hydroxide with compounds of formula XII in which $R_{14}$ and $R_{15}$ are both H or in which $R_{14}$ is benzoyl and $R_{15}$ is H in the presence of lead acetate.

Compounds of formula XIV may be prepared by the reaction of thioureas of formula XV in which $R_{14}$ and $R_{15}$ are H (a) with sodium chlorite in the presence of a base such as sodium carbonate and a copper catalyst such as a mixture of cuprous and cupric chlorides or (b) with potassium hydroxide in the presence of lead acetate.

Thioureas of formula XV in which $R_{14}$ and $R_{15}$ are H may be prepared by the reaction of ammonia with an isothiocyanate of formula XVIII

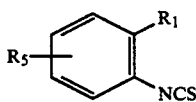

XVIII

Compounds of formula XV in which $R_{14}$ is an alkyl group and $R_{15}$ is H may be prepared by the reaction of an aminophenyl of formula VI with an alkylisothiocyanate of formula $R_{14}NCS$.

Carbodiimides of formula XVI may be prepared by the reaction of a thiourea of formula XV in which $R_{14}$ is the group $R_4$ and $R_{15}$ is H with sodium chlorite.

Compounds of formula XVIII may be prepared by the reaction of a compound of formula VI with thiophosgene in a liquid reaction medium such as dioxan.

The hypoglycaemic activity of the compounds of formula I which are given in the following Examples has been demonstrated by the following test. Rats weighing between 150 and 200 g were fasted for 18 hours and then were subcutaneously injected with glucose (800 mg/4 ml/kg) followed by an oral dose of the compound to be tested (x mg in either 4 or 5 ml of 0.2% Agar/kg). After 2 and 4 hours blood was collected by orbital bleeding and the plasma glucose estimated on a Beckman glucose analyser using the specific glucose oxidase method (Kadish A. H., Little R. L. and Sternberg J. C., Clin chem 14 116 [1968]). The percentage reduction of plasma glucose when compared to control animals which had not been given the compound to be tested, but which had been given 0.2% Agar homogenate, was then calculated. Compounds are considered to have hypoglycaemic activity in this test if they show a 15% or greater reduction in plasma glucose at any value of x up to 200 at either or both of 2 and 4 hours.

The results obtained at any value of x in the above tests were then reviewed and the hypoglycaemic activity of each compound was classified on the following scale. Where more than one set of results is available at a particular value of x, the mean value of the % reduction is used to classify the activity of the compounds.

A greater than 25% reduction at both 2 and 4 hours.

B greater than 25% reduction at 2 hours but less than 25% reduction at 4 hours.

C reduction in the range 15 to 25% at 2 hours but greater than 25% reduction at 4 hours.

D reduction in the range 15 to 25% at both 2 and 4 hours.

E reduction in the range 15 to 25% at 2 hours but less than 15% reduction at 4 hours.

F less than 15% reduction at 2 hours but greater than 15% reduction at 4 hours.

The activities of the final products of each of the Examples hereinafter are given below in Table A.

TABLE A

| Example | x | Activity | Example | x | Activity |
|---|---|---|---|---|---|
| 1 | 100 | B | 2 | 25 | A |
| 3 | 36 | F | 4 | 25 | E |
| 5 | 37 | A | 6 | 35 | B |
| 7 | 35 | B | 8 | 37 | A |
| 9 | 37 | B | 10 | 36 | D |
| 11 | 35 | B | 12 | 34 | B |
| 13 | 200 | E | 14 | 200 | D |
| 15 | 200 | E | 16 | 200 | A |
| 17 | 80 | D | 18 | 200 | E |
| 19 | 200 | D | 20 | 25 | D |
| 21 | 25 | D | 22 | 25 | B |
| 23 | 25 | D | 24 | 200 | E |
| 25 | 200 | A | 26 | 200 | E |
| 27 | 200 | D | 28 | 200 | A |
| 29 | 25 | B | 30 | 25 | B |
| 31 | 25 | A | 32 | 35 | A |
| 33 | 200 | A | 34 | 25 | B |
| 35 | 200 | A | 36 | 25 | C |
| 37 | 200 | E | 38 | 35 | B |
| 39 | 25 | D | 40 | 25 | B |
| 41 | 34 | B | 42 | 35 | B |
| 43 | 25 | F | 44 | 25 | A |
| 45 | 200 | B | 46 | 32 | E |
| 47 | 25 | B | 48 | 200 | E |
| 49 | 25 | A | 50 | 200 | B |
| 51 | 200 | A | 52 | 25 | B |
| 53 | 200 | A | 54 | 25 | B |
| 55 | 25 | C | 56 | 25 | A |
| 57 | 25 | D | 58 | 25 | B |
| 59 | 160 | D | 60 | 200 | B |
| 61 | 25 | D | 62 | 200 | B |
| 63 | 200 | B | 64 | 200 | D |
| 65 | 25 | A | 66 | 200 | C |
| 67 | 25 | D | 68 | 25 | A |
| 69 | 44 | B | 70 | 34 | A |
| 71 | 25 | B | 72 | 25 | B |
| 73 | 25 | B | 74 | 25 | D |
| 75 | 25 | B | 76 | 200 | B |

The invention will now be illustrated by the following description of several Examples thereof. Each of the compounds was characterised by standard laboratory techniques which include elemental analyses and spectroscopy. The product of each Example has been shown to have hypoglycaemic activity in the test described hereinbefore.

EXAMPLE 1

A mixture of 2-piperidone (4 g) in benzene (40 ml), 2-aminobiphenyl (3.3 g) in benzene (15 ml) and phosphorus oxychloride (3.7 ml) was heated at 60°–65° C. for 5 hours to yield an oil which was dissolved in methanol. Treatment with 57% hydriodic acid gave 2-(2-piperidinylideneamino)biphenyl hydriodide (m.p. 172° C.) which was recrystallised from a 1:2 mixture of methanol and ether.

EXAMPLE 2

A mixture of 1,3-dimethyl-2-imidazolidinone (5.5 g) in benzene (30 ml), 2-aminobiphenyl (5.1 g) in benzene (20 ml) and phosphorus oxychloride (4.4 ml) was heated at 80°–85° C. for 20 hours to yield 2-(1,3-dimethyl-2-imidazolidinylideneamino)biphenyl (m.p. 90°–91° C.) which was recrystallised from hexane.

EXAMPLE 3

A mixture of N-methylpivalamide (4.8 g) in benzene (50 ml), 2-aminobiphenyl (5 g) in benzene (25 ml) and phosphorous oxychloride (3.9 ml) was heated at 65°–70° C. for 12 hours to yield a solid (m.p. 70°–71° C.) which was recrystallised from hexane. The solid was dissolved in methanol (25 ml) and treated with fumaric acid to give N-(2-biphenylyl)-N'-methylpivalamidine fumarate (m.p. 164°–165° C.) which was recrystallised from a 1:1 mixture of methanol and ether.

EXAMPLE 4

A mixture of 2-aminobiphenyl (3.4 g), cyclohexane carbonitrile (6.5 g) and anhydrous aluminium chloride (8 g) was heated at 100° C. for 8 hours then at 120° C. for 8 hours to yield a product which was purified by chromatography on a neutral alumina column which was eluted with dichloromethane to give N-(2-biphenylyl)-cyclohexane-1-carboxamidine (m.p. 148°–150° C.).

EXAMPLE 5

A mixture of 2-aminobiphenyl (10.2 g), thiophosgene (10.4 g), dioxane (50 ml) and water (100 ml) was prepared with cooling in an ice bath. The temperature was raised to 30° C. and stirred for 3 hours at 30° C. to yield 2-biphenylylisothiocyanate as a yellow oil.

Treatment of 2-biphenylylisothiocyanate (10.2 g) with a saturated solution of ammonia in ethanol (100 ml) at 10 to 30° C. for 4 hours and then at 30° C. for 16 hours yielded N-(2-biphenylyl)thiourea (m.p. 183°–184° C.).

A mixture of N-(2-biphenylyl)thiourea (9.6 g), methyl iodide (2.9 ml) and acetone (100 ml) was heated at 55° C. for 3 hours to yield 1-(2-biphenylyl)-2-methyl-2-thiopseudourea hydriodide.

A mixture of 1-(2-biphenylyl)-2-methyl-2-thiopseudourea hydriodide (5.6 g) and N-methylethylenediamine (3.3 g) in ethanol (70 ml) was heated under reflux for 48 hours. Removal of the solvent gave an oil which was dissolved in methanol (25 ml) and treated with fumaric acid (1.7 g) to give 2-(1-methyl-2-imidazolidinylideneamino)biphenyl fumarate (m.p. 168°–169° C.) which was recrystallised from a 1:1 mixture of methanol and ether.

EXAMPLE 6

A mixture of 1-(2-biphenylyl)-2-methyl-2-thio pseudourea hydriodide (6.5 g prepared as described in Example 5) and N-(n-butyl)ethylenediamine (6.1 g) in ethanol (75 ml) was heated under reflux for 75 hours. Removal of the solvent gave an oil which was distilled (b.p. 183 at 2 mm Hg). The distillate was dissolved in methanol and treated with fumaric acid to give 2-(1-n-butyl-2-imidazolidinylideneamino)biphenyl fumarate (m.p. 120°–121° C.) which was recrystallised from a 1:1 mixture of propan-2-ol and ether.

EXAMPLE 7

A mixture of 1-(2-biphenylyl)-2-methyl-2-thiopseudourea hydriodide (12 g prepared as described in Example 5) and N-(2-hydroxyethyl)ethylenediamine (10 g) in ethanol (145 ml) was heated under reflux for 165 hours. Removal of the solvent gave an oil which was dissolved in methanol and treated with fumaric acid to give 2-[1-(2-hydroxyethyl)-2-imidazolidinylidene]-aminobiphenyl fumarate (m.p. 165°–166° C.) which was recrystallised from a 1:2 mixture of methanol and ether.

EXAMPLE 8

A mixture of 2-aminobiphenyl (6.3 g), methylisothiocyanate (3.8 g) and dichloromethane (45 ml) was stirred at ambient temperature for four days to give N-(2-biphenylyl)-N'-methylthiourea (m.p. 152°–153° C.).

A mixture of N-(2-biphenylyl)-N'-methylthiourea (10.5 g), methyl iodide (6.8 g) and acetone (75 ml) was heated under reflux for 2.5 hours to give 1-(2-biphenylyl)-2,3-dimethyl-2-thiopseudourea hydriodide.

A mixture of 1-(2-biphenylyl)-2,3-dimethyl-2-thiopseudourea hydriodide (7 g) and a 33% solution of methylamine in ethanol (250 ml) was stirred at ambient temperature for 56 days to give N-(2-biphenylyl)-N',N''-dimethylguanidine (m.p. 101°–102° C.) which was recrystallised from hexane. A sample (2.4 g) was dissolved in methanol (25 ml) and treated with fumaric acid (1.16 g) to give N-(2-biphenylyl)-N',N''-dimethylguanidine fumarate (m.p. 192°–193° C.) which was recrystallised from propan-2-ol.

EXAMPLE 9

A mixture of 2-aminobiphenyl hydrochloride (9.2 g) and N,N-dimethylcyanamide (4.8 g) in m-cresol (30 ml) was heated at 90°–95° C. for 10 hours to yield an oil which was dissolved in methanol (60 ml) and treated with fumaric acid (4.5 g) to give N-(2-biphenylyl)-N',N'-dimethylguanidine fumarate (m.p. 175°–176° C.) which was recrystallised from a 2:3 mixture of methanol and ether.

EXAMPLE 10

A mixture of 2-amino-4-methoxybiphenyl hydrochloride (7 g) and N,N-dimethylcyanamide (3.1 g) in m-cresol (40 ml) was heated at 90°–95° C. for 28 hours to yield N'-(4-methoxy-2-biphenylyl)-N',N'-dimethylguanidine (m.p. 146°–148° C.) which was recrystallised from hexane. A sample (1.7 g) was dissolved in methanol (10 ml) and treated with fumaric acid (0.7 g) to give N-(4-methoxy-2-biphenylyl)-N',N'-dimethyl guanidine fumarate [m.p. 170° C. (dec)] which was recrystallised from a 1:3 mixture of methanol and ether.

EXAMPLE 11

A mixture of 2-aminobiphenyl hydrochloride (6.17 g) and 4-cyanomorpholine (5.05 g) in m-cresol (25 ml) was heated at 90°–95° C. for 15 hours to yield N-(2-biphenylyl)-4-morpholine carboxamidine (m.p. 153°–154° C.) which was recrystallised from ethylacetate. N-(2-Biphenylyl)morpholine-4-carboxamidine (3.5 g) was dissolved in methanol (15 ml) and treated with fumaric acid (1.45 g) to give N-(2-biphenylyl)morpholine-4-carboxamidine fumarate (m.p. 222°–223° C.) which was recrystallised from a 1:1 mixture of methanol and ether.

EXAMPLE 12

A mixture of 2-amino-4-methoxybiphenyl hydrochloride (4.4 g) and 4-cyanomorpholine (3.14 g) in m-cresol (25 ml) was heated at 90°–95° C. for 20 hours to yield N-(4-methoxy-2-biphenylyl)morpholine-4-carboxamidine (m.p. 140°–142° C.) which was recrystallised from ethylacetate. N-(4-Methoxy-2-biphenylyl)morpholine-4-carboxamidine (1.2 g) was dissolved in methanol (10 ml) and treated with fumaric acid (1.45 g) to give N-(4-methoxy-2-biphenylyl)morpholine-4-carboxamidine fumarate [m.p. 120° (dec)] which was recrystallised from a 1:1 mixture of methanol and ether.

EXAMPLE 13

A cold (5° C.) slurry of N-acetyl-m-anisidine (1.65 g) and silver nitrate (1.69 g) in trichloromethane (10 ml) was treated dropwise with trifluoroacetic anhydride (5 ml). After stirring at 5° C. for 6 hours and at 23° C. for 12 hours, the reaction mixture was poured onto ice/water. Extraction of the sticky residue in dichloromethane gave a solid which was purified on a silica column using ethylacetate-hexane as eluant to furnish N-acetyl-2-nitro-5-methoxyaniline as golden yellow needles (m.p. 129° C.). N-deacetylation was effected by refluxing ethanolic sodium hydroxide (0.3 g) in (10 ml) ethanol to give 2-nitro-5-methoxyaniline (m.p. 115° C.).

A suspension of 2-nitro-5-methoxyaniline (3.7 g) in water (25 ml) was heated at 80° C. with 36% hydrochloric acid (7.7 ml) for 30 minutes. It was then treated dropwise with aqueous sodium nitrite solution (1.8 g in 5 ml H$_2$O) at 0° C. After 1 hour, the mixture was filtered and the filtrate added at 23° C. to a solution of dimethylamine (35% aqueous solution, 3.9 ml) and sodium carbonate (8.2 g) in water (340 ml). After 12 hours at 23° C. a solid was collected by filtration and dissolved in benzene (100 ml). The solution was heated under reflux and treated with p-toluene sulphonic acid (4.0 g) and heated under reflux for 4 hours in a Dean-Stark water separator. The reaction mixture stood for 48 hours and was then partitioned between cold 10% aqueous sodium hydroxide solution and dichloromethane. Evaporation of the organic layer left an oil which was purified on silica column using ethylacetate:hexane as eluant to furnish 5-methoxy-2-nitrobiphenyl which was dissolved in ethanol (30 ml) and heated under reflux with sodium sulphide (5.3 g) for 8 hours. Purification of the product on a silica column gave 2-amino-5-methoxybiphenyl which was converted into its hydro-chloride salt (m.p. 167° C.).

2-Amino-5-methoxybiphenyl hydrochloride (0.9 g) was heated with N-cyanopiperidine (0.45 g) in m-cresol (1 ml) at 140° C. for 8 hours to give N-(5-methoxy-2-biphenylyl)piperidine-1-carboxamidine which was crystallised from a 1:9 mixture of ethylacetate and hexane to furnish N-(5-methoxy-2-biphenylyl)piperidine-1-carboxamidine as a pale brown crystals (m.p. 155° C.).

EXAMPLE 14

A mixture of 2-amino-3'-methylbiphenyl hydrochloride (1.09 g), N-cyanopiperidine (0.6 g) and m-cresol (0.5 ml) was heated at 100° C. for 3 hours to give N-(3'-methyl-2-biphenylyl)piperidine-1-carboxamidine (m.p. 131° C.).

EXAMPLE 15

A mixture of 4-methanesulphonyliodobenzene (18 g), 2-bromonitrobenzene (12.7 g) and copper powder (12 g) was heated at 120° C. for 30 hours to yield a residue which was purified by chromatography on a silica column eluted successively with 5:95 mixture, a 10:90 mixture, a 25:75 mixture and then a 40:60 mixture of ethylacetate and hexane to give 4'-methanesulphonyl-2-nitrobiphenyl (m.p. 178° C.). 4'-methanesulphonyl-2-nitrobiphenyl (5 g) was heated at 90°-95° C. for 6 hours with hydrated sodium sulphide (17.3 g) and ethanol (100 ml) to give 2-amino-4'-methanesulphonylbiphenyl (m.p. 164°-165° C.).

A mixture of 2-amino-4'-methanesulphonylbiphenyl hydrochloride (2.3 g), N-cyanopiperidine (1.3 g) and m-cresol (10 ml) was heated at 90°-95° C. for 10 hours to give N-(4'-methanesulphonyl-2-biphenylyl)piperidine-1-carboxamidine (m.p. 128°-129° C.) which was recrystallised from hexane.

EXAMPLE 16

A mixture of 2-amino-4-methylbiphenyl hydrochloride (7.7 g) and 4-cyanomorpholine (5.9 g) in m-cresol (45 ml) was heated at 90°-95° C. for 15 hours to yield N-(4-methyl-2-biphenylyl)morpholine-4-carboxamidine (m.p. 154°-155° C.) which was recrystallised from hexane.

EXAMPLE 17

2-Amino-5-methoxybiphenyl hydrochloride (0.4 g) was heated with N,N-dimethylcyanamide (0.3 ml) in m-cresol (0.5 ml) at 110° C. for 8 hours to give a residue which was triturated with ether and crystallised from a 1:1 mixture of acetone and ether to give N-(5-methoxy-2-biphenylyl)-N',N'-dimethyl guanidine hydrochloride (m.p. 160° C.).

EXAMPLE 18

A solution of bromine (1.7 ml) in methanol (20 ml) was saturated with potassium bromide and added over 1 hour to a solution of potassium thiocyanate (7.3 g) and 2-biphenylamine (5.07 g) in methanol (80 ml) at −5° C. After 1 hour at 23° C., the reaction mixture was poured into a mixture of ice and water and the pH was adjusted to 8 by the addition of solid sodium bicarbonate. Extraction with dichloromethane gave 2-aminobiphenyl-5-thiocyanate.

To a solution of 2-aminobiphenyl-5-thiocyanate (11.06 g), in ethanol (260 ml) at 15° C., was added sodium borohydride (3.0 g) over 15 minutes. The mixture was heated under reflux for 15 minutes. 85% Aqueous potassium hydroxide solution (3.2 g) was diluted with ethanol (60 ml) and added dropwise at 10° C. A solution of methyl iodide (3.4 ml) in ethanol (25 ml) was added and the mixture stirred at 23° C. for 2 hours. Cold water was added and the mixture extracted with ether to give 2-amino-5-methylthiobiphenyl.

Reaction of 2-amino-5-methylthiobiphenyl hydrochloride (1.6 g) with N,N-dimethylcyanamide (0.83 g) in m-cresol (1 ml) at 80° C. for 6 hours yielded a colourless solid which was dissolved in methanol (50 ml) and treated with a solution of fumaric acid (0.61 g) in methanol (50 ml) to give N,N-dimethyl-N'-(5-methylthio-2-biphenylyl)guanidine hemifumarate as a colourless solid (m.p. 207° C.).

EXAMPLE 19

To a stirred and cooled (0° C.) solution of 4'-acetyl-2-nitrobiphenyl (3 g, prepared as described in J Chem Soc C 840 1966) in ethylacetate (100 ml), was added stannous chloride (13.1 g) in small portions over 15 minutes. After stirring at ambient temperature for 10 hours, the reaction mixture was partitioned between 20% aqueous sodium hydroxide solution (40 ml) and ethyl acetate (100 ml). The organic layer was washed with brine, dried (Na$_2$SO$_4$) and the solvent removed by evaporation to give a residue which was converted into 4'-acetyl-2-aminobiphenyl hydrochloride.

Reaction of dry 4'-acetyl-2-aminobiphenyl hydrochloride (2.6 g) with N,N-dimethylcyanamide (2.5 ml) in m-cresol (7 ml) at 80° C. for 5 hours gave N-(4'-acetyl-2-biphenylyl)-N',N'-dimethylguanidine (2.3 g) as a colourless solid (m.p. 174°-175° C.) which was recrystallised from a mixture of acetone and hexane.

Reaction of the free base (1.3 g) in methanol (5 ml) with fumaric acid (0.54 g) in methanol (2 ml) gave N-(4'-acetyl-2-biphenylyl)-N',N'-dimethylguanidine fumarate as a colourless solid (m.p. 194°-195° C.) which was recrystallised from methanol.

EXAMPLE 20

3-Methyl-2-nitrobiphenyl (1 g) was heated at 90°–95° C. for 28 hours with hydrated sodium sulphide (4.5 g) and ethanol (25 ml) to give 2-amino-3-methyl-biphenyl (m.p. 66°–67° C.) which was recrystallised from hexane and converted into its hydrochloride salt.

A mixture of 2-amino-3-methylbiphenyl hydrochloride (2.65 g), N,N-dimethylcyanamide (1.3 g) and m-cresol (20 ml) was heated at 90°–95° C. for 18 hours to give N,N-dimethyl-N'-(3-methyl-2-biphenylyl)guanidine as a colourless solid (m.p. 144°–145° C.) which was recrystallised from hexane.

EXAMPLE 21

A mixture of 2-amino-6-methylbiphenyl hydrochloride (2.98 g), N,N-dimethylcyanamide (1.46 g) and m-cresol (25 ml) was heated at 90°–95° C. for 6 hours to give N,N-dimethyl-N'-(6-methyl-2-biphenylyl)guanidine (m.p. 181°–182° C.) which was recrystallised from hexane.

EXAMPLE 22

A mixture of 2-amino-5-fluorobiphenyl hydrochloride (3.6 g), N,N-dimethylcyanamide (1.68 g) and m-cresol (25 ml) was heated at 90°–95° C. for 8 hours to give N-(5-fluoro-2-biphenylyl)-N',N'-dimethylguanidine (m.p. 160°–161° C.) which was recrystallised from hexane.

EXAMPLE 23

A mixture of 2-amino-3'-fluorobiphenyl hydrochloride (3.6 g), N,N-dimethylcyanamide (1.7 g) and m-cresol (25 ml) was heated at 90°–95° C. for 8 hours to give N-(3'-fluoro-2-biphenylyl)-N',N'-dimethyl guanidine (m.p. 109°–110° C.) as a colourless solid which was recrystallised from hexane.

EXAMPLE 24

A mixture of 2-amino-3'-methylbiphenyl hydrochloride (1 g), N,N-dimethylcyanamide (0.67 ml) in m-cresol (1 ml) was heated at 100° C. for 3 hours to give N,N-dimethyl-N'-(3'-methyl-2-biphenylyl)guanidine (m.p. 116° C.) which was crystallised from hexane.

EXAMPLE 25

A mixture of 2-amino-4'-methanesulphonylbiphenyl hydrochloride (3.3 g), N,N-dimethylcyanamide (1.55 ml) and m-cresol (10 ml) was heated at 90°–95° C. for 14 hours to give N,N-dimethyl-N'-(4'-methanesulphonyl-2-biphenyl) guanidine (m.p. 94°–95° C.) which was recrystallised from hexane.

EXAMPLE 26

A mixture of 2-amino-4'-methylbiphenyl hydrochloride (5.3 g), N,N-dimethylcyanamide (2.55 g) and m-cresol (25 ml) was heated at 90°–95° C. for 10 hours to give N,N-dimethyl-N'-(4'-methyl-2-biphenylyl)guanidine (m.p. 147°–148° C.) which was recrystallised from hexane.

EXAMPLE 27

A solution of potassium hydroxide (20.2 g) in ethanol (250 ml) was added with stirring to a solution of 4-nitrophenol (50 g) in ethanol (250 ml). Benzyl bromide (60.71 g) was added dropwise and the mixture heated under reflux for 3 hours and then stood overnight. A solid was separated by filtration, washed with ethanol, suspended in water for 30 minutes and collected by filtration and dried in vacuo. The solid was 4-benzyloxynitrobenzene.

Sodium hydrogen sulphide monohydrate (40 g) was added to a solution of 4-benzyloxynitrobenzene (25 g) in ethanol (800 ml) and the reaction mixture heated under reflux for four hours. The solvent was removed and the residue was treated with water and extracted into ether. The ether extract was dried and evaporated to give 4-benzyloxyaniline which was purified by extraction with hexane.

Thiophosgene (12.63 g) was added at 0° C. to a stirred suspension of calcium carbonate (11.05 g) in a mixture of dichloromethane (100 ml) and water (100 ml). A solution of p-benzyloxyaniline (16.5 g) in dichloromethane (100 ml) was added dropwise at 0° C. over 30 minutes. The mixture was stirred for four hours at 15° C. The organic layer was separated, dried and the solvent removed by evaporation to give a residue which was extracted into boiling hexane to give 4-benzyloxyphenylisothiocyanate (m.p. 69° C.).

25% Aqueous ammonia solution (150 ml) was added to a solution of 4-benzyloxyphenylisothiocyanate (17.3 g) in ethanol (100 ml) at 10° C. and the mixture stirred for 6 hours and stood overnight. N-(4-benzyloxyphenyl)thiourea (m.p. 184°–185° C.) was collected by filtration and dried by suction.

A hot solution of potassium hydroxide (25.2 g) in water (70 ml) was added to N-(4-benzyloxyphenyl)thiourea (11.34 g) suspended in boiling water (80 ml). A hot solution of lead acetate trihydrate (71.5 g) in water (80 ml) was added and the mixture heated under reflux for an hour and filtered whilst hot. The filtrate was cooled, acidified to pH 7 with acetic acid and extracted with dichloromethane to give 4-benzyloxyphenylcyanamide as a white solid which was purified by flash chromatography (as described by Still et al in J Org Chem, 1978, 43, 2923–2925) over silica using hexane and chloroform as eluant to give 4-benzyloxyphenylcyanamide (m.p. 105° C.).

Potassium carbonate (9.6 g) was added to a solution of 4-benzyloxyphenylcyanamide (6.3 g) in acetone (450 ml) with stirring. A solution of methyl-4-toluene sulphonate (9 g) in acetone (50 ml) was added and the mixture stirred for 7 hours. The solvent was removed by evaporation and the residue suspended in water and extracted into dichloromethane. The extract was dried ($Na_2SO_4$) and the solvent removed by evaporation to give a residue which was triturated with a 1:1 mixture of ethylacetate and hexane to give N-methyl-4-benzyloxyphenylcyanamide (m.p. 116° C.).

N-Methyl-4-benzyloxyphenylcyanamide (3.6 g) was added to a suspension of 2-aminobiphenyl hydrochloride (3 g) in m-cresol (8 ml) and the mixture was heated at 90°–95° C. for 3 hours and then added to water. The aqueous layer was basified with solid sodium bicarbonate and extracted with ether. The extract was dried ($Na_2SO_4$) and the solvent removed to give a residue which was extracted into boiling hexane to yield N-(4-benzyloxyphenyl)-N'-(2-biphenylyl)-N-methylguanidine.

Reaction of N-(4-benzyloxyphenyl)-N'-(2-biphenylyl)-N-methylguanidine (3 g) in methanol (150 ml) with hydrogen at 40 lb. in$^{-2}$ in the presence of 10% palladium/charcoal (1 g) for 8 hours gave N-(2-biphenyl)-N'-(4-hydroxyphenyl)-N'-methyl-guanidine which was converted into its fumarate salt (m.p. 212° C.) which was crystallised from a 1:1 mixture of methanol and ether.

EXAMPLE 28

A mixture of 3-methylthioiodobenzene (30 g), 2-nitrobromobenzene (24 g) and copper powder (23 g) was heated at 120° C. for 34 hours to yield a residue which was purified by chromatography on a silica column eluted with hexane to give 3'-methylthio-2-nitrobiphenyl (m.p. 42°–43° C.).

3'-Methylthio-2-nitrobiphenyl (8 g) was heated at 90°–95° C. for 5 hours with hydrated sodium sulphide (15.6 g) and ethanol (200 ml) to give 2-amino-3'-methylthiobiphenyl (m.p. 114°–115° C.) as a brown oil which was converted into its hydrochloride salt.

A mixture of 2-amino-3'-methylthiobiphenyl hydrochloride (3.3 g), N,N-dimethylcyanamide (1.55 ml) and m-cresol (10 ml) was heated at 90°–95° C. for 14 hours to give N,N-dimethyl-N'-(3'-methylthio-2-biphenylyl)-guanidine (m.p. 94°–95° C.) which was recrystallised from hexane.

EXAMPLES 29 TO 63

A mixture of a compound of formula XIV in which $R_1$ is phenyl (A g prepared as described hereinafter in Preparative Procedures A to G), an amine of formula $HNR_3R_4$ (B g) and ethanol (C ml) was heated at 90°–95° C. on a steam bath for D hours to yield the products identified in Table 1. The notes to Table 1 are:

(1) The free base recrystallised from ethylacetate.
(2) The free base recrystallised from hexane.
(3) The free base was converted into its fumarate salt which was recrystallised from methanol. The melting point of this salt is given in Table 1.
(4) The free base was recrystallised from a 1:1 mixture of ethylacetate and hexane.
(5) The reaction yielded an oil which was purified on an alumina column using hexane, a 1:1 mixture of ethylacetate and hexane and then ethylacetate as eluant to give the free base which was converted into its fumarate salt which was crystallised from an 1:1 mixture of acetone and ether.
(6) The reaction mixture was heated at 55°–60° C. for 8 hours.
(7) The free base was converted into its fumarate salt which was recrystallised from a 1:2 mixture of methanol and ether.
(8) The free base was converted into its fumarate salt which was recrystallised from propan-2-ol and isolated as a hemihydrate.
(9) The product was isolated as it ¾ fumarate salt.
(10) The product was converted into its hemifumarate salt which was recrystallised from a 1:3 mixture of methanol and ether and isolated as a hemihydrate.
(11) The reaction mixture was heated at 55°–60° C. for 16 hours.
(12) After the reaction mixture had been heated for 2 hours at 90°–95° C., 4-dimethylaminopyridine (80 mg) was added and heating was then continued for a further four hours.
(13) The free base was recrystallised from a 3:2 mixture of ethyl acetate and hexane.
(14) The reaction yielded a solid which was purified by chromatography on an alumina column using dichloromethane and then a 98:2 mixture of dichloromethane and methanol as eluant and crystallised from ethylacetate.
(15) The product was extracted with dichloromethane and then with hexane to give colourless crystals.
(16) The reaction was performed in dimethoxyethane.
(17) The free base was converted into its fumarate salt which was recrystallised from a 1:1 mixture of methanol and ether.
(18) The free base was treated with 2 equivalents of fumaric acid to give a hygroscopic solid, the melting point of which was not measured.

TABLE 1

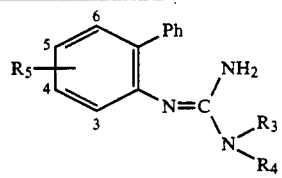

TABLE 1

| Ex | $R_5$ | $NHR_3R_4$ | A | B | C | D | m.p. °C. | Notes |
|---|---|---|---|---|---|---|---|---|
| 29 | H | piperidine | 4 | 2.1 | 30 | 6 | 123–124 | (1) |
| 30 | H | 1,2,5,6-tetrahydropyridine | 3 | 1.54 | 30 | 2 | 111–112 | (2) |
| 31 | H | 4-methylpiperidine | 3 | 2.3 | 40 | 10 | 110–112 | (2) |
| 32 | H | 4-hydroxypiperidine | 5.3 | 3.4 | 30 | 8 | 218–219 | (3) |
| 33 | 4-F | 4-hydroxypiperidine | 3 | 1.7 | 30 | 2 | 150–152 | (1) |
| 34 | 5-F | 4-hydroxypiperidine | 2.8 | 1.5 | 25 | 5 | 146–147 | (1)(16) |
| 35 | 3-Me | 4-hydroxypiperidine | 3 | 1 | 30 | 15 | 186–187 | (1)(16) |
| 36 | 5-Me | 4-hydroxypiperidine | 3 | 1.75 | 30 | 1 | 144–145 | (4) |
| 37 | 4-SMe | 4-hydroxypiperidine | 2.4 | 1.2 | 30 | 1 | 128–129 | (1) |
| 38 | 5-SMe | 4-hydroxypiperidine | 1.2 | 1.5 | 2 | 6 | 100(dec) | (5) |
| 39 | H | 4-methoxypiperidine | 1.7 | 2 | 20 | 1 | 133–134 | (2) |
| 40 | H | 3-methoxypiperidine | 2.8 | 2 | 20 |  | 116–118 | (2)(6) |
| 41 | H | 3-hydroxymethyl piperidine | 1.5 | 2 | 20 | 0.75 | 202–204 | (7) |
| 42 | H | 4-hydroxymethylpiperidine | 2.8 | 2 | 25 | 1 | 160–162 | (8) |
| 43 | H | 4-methyoxyimino-piperidine | 1.5 | 2 | 20 |  | 168–169 | (2)(11) |
| 44 | H | 4-hydroxy-4-methyl-piperidine | 2.3 | 1.5 | 25 | 2 | 134–136 | (1) |
| 45 | H | 4-dimethylcarbamoyl-piperidine | 3 | 2.9 | 30 | 3 | 159–160 | (1) |
| 46 | 5-SMe | morpholine | 1.8 | 1 | 25 | 6 | 95 | (9) |
| 47 | H | 2-methylmorpholine | 3 | 2 | 25 | 2 | 140–142 | (4) |

TABLE 1-continued

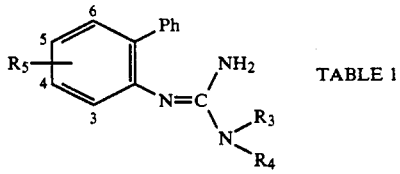

TABLE 1

| Ex | R5 | NHR3R4 | A | B | C | D | m.p. °C. | Notes |
|---|---|---|---|---|---|---|---|---|
| 48 | H | 3,3-dimethylmorpholine | 3.9 | 4.6 | 40 | 2 | 185–186 | (10) |
| 49 | H | thiomorpholine | 4 | 2.6 | 30 | 5 | 148–149 | (1) |
| 50 | H | thiomorpholine-1,1-dioxide | 2.4 | 2 | 20 | | 218–220 | (1)(12) |
| 51 | H | 3-hydroxypyrrolidine | 3.7 | 2 | 20 | 2 | 90–92 | (13) |
| 52 | H | 1-methylpiperazine | 3 | 3 | 40 | 6 | 128–130 | (2) |
| 53 | 4-F | 1-methylpiperazine | 3 | 3 | 30 | 3 | 143–145 | (2) |
| 54 | 5-F | 1-methylpiperazine | 2.7 | 1.4 | 25 | 5 | 112–113 | (2)(16) |
| 55 | 3-Me | 1-methylpiperazine | 3 | 1.4 | 30 | 18.5 | 115–116 | (14)(16) |
| 56 | 5-Me | 1-methylpiperazine | 1.7 | 1.8 | 20 | 1 | 118–120 | (2) |
| 57 | 4-SMe | 1-methylpiperazine | 3 | 2.5 | 30 | 1 | 152–153 | (1) |
| 58 | 5-SMe | 1-methylpiperazine | 2 | 1.8 | 25 | 5 | 89 | (15) |
| 59 | H | 1-ethylpiperazine | 3.5 | 2.5 | 30 | 8 | 145–147 | (2) |
| 60 | H | 1-(2-hydroxyethyl)piperazine | 1.5 | 2 | 20 | 2 | 136–137 | (1) |
| 61 | H | 2-(2-methylaminoethyl)-pyridine | 3 | 2.7 | 25 | 4 | 102–104 | (2) |
| 62 | H | N-ethyl-2-methoxyethylamine | 3.88 | 2 | 30 | 2.5 | 71–72 | (16)(17) |
| 63 | H | N-methyl-N-(2-dimethylaminoethyl)amine | 3 | 2.05 | 30 | 4 | | (18) |

Preparative Procedure A

Reaction of 2-aminobiphenyl (10 g) with thiophosgene (10.2 g) in a mixture of dioxane (15 ml) and water (50 ml) at 0°–5° C. for 30 minutes and at ambient temperature for 2 hours with stirring gave 2-biphenylylisothiocyanate as a yellow oil.

Reaction of 2-biphenylyl isothiocyanate (9.1 g) in ethanol (25 ml) with 25% aqueous ammonia solution (50 ml) at ambient temperature for 18 hours gave N-(2-biphenylyl)thiourea (m.p. 187°–188° C.).

A suspension of N-(2-biphenylyl)thiourea (7.8 g) in water (60 ml) was reacted with a solution of potassium hydroxide (19.15 g) in water (60 ml), lead acetate trihydrate (12.96) in water (60 ml) was added and the reaction mixture heated at 90°–95° C. for 30 minutes and filtered. The filtrate was acidified with acetic acid with cooling to yield 2-biphenylylcyanamide as a colourless solid (m.p. 85°–87° C.).

Preparative Procedure B

A mixture of benzoylisothiocyanate (8.78 g), 2-amino-3-methylbiphenyl (9.85 g) and dichloromethane (75 ml) at ambient temperature for two hours gave N-benzoyl-N'-(3-methyl-2-biphenylyl)thiourea (m.p. 172°–173° C.).

A mixture of N-benzoyl-N'-(3-methyl-2-biphenylyl)thiourea (16.2 g), sodium hydroxide (2 g) and ethanol was heated under reflux for two hours to give N-(3-methyl-2-biphenylyl)thiourea as a foamy solid.

A mixture of N-(3-methyl-2-biphenylyl)thiourea (11.3 g), lead acetate trihydrate (17.7 g), potassium hydroxide (26.1 g) and water (50 ml) was heated at 90°–95° C. for 30 minutes to give 3-methyl-2-biphenylylcyanamide as a yellow oil.

Preparative Procedure C

Reaction of 2-amino-4-fluorobiphenyl (9.6 g) in a mixture of dioxan (20 ml) and water (100 ml) at 0°–5° C. (30 minutes) and at ambient temperature for 2 hours yielded 4-fluoro-2-biphenylyl isothiocyanate as a pale yellow oil.

Reaction of 4-fluoro-2-biphenylylisothiocyanate (12 g) in ethanol (10 ml) with 25% aqueous ammonia solution (40 ml) at ambient temperature for 8 hours gave N-(4-fluoro-2-biphenylyl)thiourea as a white solid (m.p. 185°–187° C.).

A suspension of N-(4-fluoro-2-biphenylyl)thiourea (11 g) in water (70 ml) was reacted with a solution of potassium hydroxide (25.2 g) in water (70 ml). Lead acetate trihydrate (17 g) in water (70 ml) was added and the reaction mixture heated at 90°–95° C. for 40 minutes to give 4-fluoro-2-biphenylylcyanamide (m.p. 68°–70° C.).

Preparative Procedure D

Reaction of 2-amino-5-fluorobiphenyl (7.8 g) with thiophosgene (7.2 g) in a mixture of dioxan (15 ml) and water (60 ml) at ambient temperature for 2 hours yielded 5-fluoro-2-biphenylylisothiocyanate as a brown oil.

Reaction of 5-fluoro-2-biphenylylisothiocyanate (9.3 g) in ethanol (40 ml) with 28% aqueous ammonia solution (80 ml) at ambient temperature for 24 hours gave N-(5-fluoro-2-biphenylyl)thiourea as a yellow solid (m.p. 188°–190° C.).

A suspension of N-(5-fluoro-2-biphenylyl)thiourea (8 g) in water (40 ml) was reacted with a solution of potassium hydroxide (18.2 g) in water (40 ml), and a solution of lead acetate trihydrate (12.3 g) in water (70 ml). The reaction mixture heated at 90°–95° C. for 1 hour to give 5-fluoro-2-biphenylylcyanamide as a yellow oil.

Preparative Procedure E

Reaction of 2-amino-5-methylbiphenyl (7 g) with thiophosgene (5.7 g) in a mixture of dioxan (20 ml) and water (50 ml) at 0°–5° C. for 30 minutes and at ambient temperature for 1 hour gave 5-methyl-2-biphenylyl isothiocyanate as a yellow oil.

Reaction of 5-methyl-2-biphenylylisothiocyanate (7.5 g) in ethanol (20 ml) with 25% aqueous ammonia solution (60 ml) at ambient temperature for 2 hours yielded N-(5-methyl-2-biphenylyl)thiourea as a colourless solid (m.p. 175°–177° C.).

A suspension of N-(5-methyl-2-biphenylyl)thiourea (6.5 g) in water (50 ml) was reacted with a solution of potassium hydroxide (15 g) in water (50 ml). Lead acetate trihydrate (10.2 g) in water (50 ml) was added and the mixture heated at 90°–95° C. for 1 hour to give 5-methyl-2-biphenylylcyanamide as a colourless solid (m.p. 80° C.).

Preparative Procedure F

A mixture of 4-methylthio-2-nitroaniline (27.6 g), amyl nitrite (22.5 ml) and cupric chloride (4.5 g) in dry benzene (250 ml) was heated under reflux for 9 hours to give 4-methylthio-2-nitrobiphenyl (m.p. 51°–52° C.).

4-Methylthio-2-nitrobiphenyl (15 g) was reduced with hydrated stannous chloride (64 g) in ethylacetate (300 ml) at ambient temperature for 15 hours to give 2-amino-4-methylthiobiphenyl as a yellow oil.

Reaction of 2-amino-4-methylthiobiphenyl (10.8 g) with thiophosgene (4.6 ml) in a mixture of dioxan (10 ml) and water (200 ml) at 10° C. and then at ambient temperature for 15 hours yielded 4-methylthio-2-biphenylylisothiocyanate as a yellow oil.

Reaction of 4-methylthio-2-biphenylylisothiocyanate (11.5 g), ethanol (100 ml) and 25% aqueous ammonia solution (20 ml) at ambient temperature for 15 hours gave N-(4-methylthio-2-biphenylyl)thiourea as a colourless solid (m.p. 166°–167° C.).

A mixture of N-(4-methylthio-2-biphenylyl)thiourea (9.6 g), potassium hydroxide (8.5 g), lead acetate trihydrate (12.5 g) and water (165 ml) was heated at 90°–95° C. for 30 minutes to give 4-methylthio-2-biphenylylcyanamide.

Preparative Procedure G

Benzoylisothiocyanate (9.44 g) was added to a solution of 2-amino-5-methylthiobiphenyl (10.3 g) in trichloromethane (120 ml) at 5° C. The mixture was kept at ambient temperature for 12 hours and the solvent partially removed. The resulting solid was suspended in hexane, separated by filtration and added to boiling aqueous sodium hydroxide solution (24.5 g in 200 ml water) to yield 5-methylthio-2-biphenylylthiourea.

A mixture of 5-methylthio-2-biphenylylthiourea (9 g) and aqueous potassium hydroxide solution (9 g in 150 ml water) was heated to boiling and a solution of lead acetate trihydrate (12.8 g) in water (85 ml) was added. The mixture was heated under reflux for one hour and filtered. The filtrate was neutralised by adding cold glacial acetic acid (4 ml) to yield 5-methylthio-2-biphenylylcyanamide (m.p. 85° C.).

EXAMPLE 64

A mixture of N-benzylpiperazine (8.8 g), methanesulphonyl chloride (4.3 ml), anhydrous potassium carbonate (20 g) in dry acetonitrile (100 ml) was stirred at ambient temperature for five hours to give N-benzyl-N'-methanesulphonylpiperazine (m.p. 115°–116° C.).

A mixture of N-benzyl-N'-methanesulphonylpiperazine (12.4 g), cyclohexane (5.1 ml), 10% Pd/C (2 g) and methanol (120 ml) was heated under reflux for 7 hours to give 1-methanesulphonylpiperazine (m.p. 90°–91° C.).

A mixture of 2-biphenylylcyanamide (3.8 g), 1-methanesulphonylpiperazine (3.8 g) and ethanol (60 ml) was heated at 90°–95° C. for 12 hours to give N-(2-biphenylyl)-4-methanesulphonylpiperazine-1-carboxamidine (m.p. 178°–180° C.) which was recrystallized from ethanol.

EXAMPLE 65

A mixture of N-(2-biphenylyl)cyanamide (2.5 g), 4-piperidone hydrochloride (5.8 g), sodium bicarbonate (4.4 g) and ethanol (30 ml) was stirred at ambient temperature for 4 days to give N-(2-biphenylyl)-4-piperidone-1-carboxamidine (m.p. 139°–140° C.) which was recrystallised from a 1:2 mixture of dimethoxyethane and hexane.

EXAMPLE 66

A mixture of 3-methanesulphonyliodobenzene (26.8 g), 2-nitrobromobenzene (19.2 g) and copper powder (18.2 g) was heated at 120° C. for 27 hours to yield a residue which was purified by chromatography on a silica column eluted initially with hexane and then with mixtures of ethylacetate and hexane in which the ethylacetate content was progressively raised to 60% to give 3'-methanesulphonyl-2-nitrobiphenyl (m.p. 124°–125° C.).

3'-Methanesulphonyl-2-nitrobiphenyl (14 g) was heated at 90°–95° C. for 10 hours with hydrated sodium sulphide (51 g) and ethanol (400 ml) to give 2-amino-3'-methanesulphonylbiphenyl (m.p. 114°–115° C.).

A mixture of benzoylisothiocyanate (4 g), 2-amino-3'-methanesulphonylbiphenyl (6.1 g) and dichloromethane (30 ml) at ambient temperature for two hours gave N-benzoyl-N'-(3'-methanesulphonyl-2-biphenylyl)thiourea (m.p. 179°–180° C.).

A mixture of N-benzoyl-N'-(3'-methanesulphonyl-2-biphenylyl)thiourea (8.2 g), sodium hydroxide (0.9 g) and ethanol (20 ml) was heated under reflux for 1.5 hours to give N-(3'-methanesulphonyl-2-biphenylyl)thiourea as a foamy solid.

A mixture of N-(3'-methanesulphonyl-2-biphenylyl)thiourea (6.1 g), lead acetate trihydrate (7.6 g), potassium hydroxide (11.2 g) and water (30 ml) was heated at 90°–95° C. for 30 minutes to give N-(3'-methanesulphonyl-2-biphenylyl)cyanamide as a yellow oil.

A mixture of N-(3'-methanesulphonyl-2-biphenylyl)cyanamide (2.7 g) and 33% ethanolic dimethylamine solution (25 ml) was heated under reflux for 3 hours to give N-(3'-methanesulphonyl-2-biphenylyl)-N',N'-dimethylguanidine (m.p. 113°–114° C.) which was recrystallised from ethylacetate.

EXAMPLE 67

Reaction of 2-amino-4'-chlorobiphenyl (8.7 g) and thiophosgene (7.4 g) in a mixture of dioxane (10 ml) and water (10 ml) at 0°–5° C. for 20 minutes and then at ambient temperature for 3 hours yielded 4'-chloro-2-biphenylylisothiocyanate (m.p. 63° C.) as a yellow solid.

Reaction of 4'-chloro-2-biphenylylisothiocyanate (7.6 g) with ethanol (100 ml) with 25% aqueous ammonia solution (15 ml) for 18 hours at ambient temperature yielded N-(4'-chloro-2-biphenylyl)thiourea (m.p. 175°–177° C.).

A suspension of N-(4'-chloro-2-biphenylyl)thiourea (7.1 g) in water (60 ml) was reacted with potassium hydroxide (15.1 g) in water (60 ml). Lead acetate trihydrate (10.3 g) in water (60 ml) was added and the mixture heated at 90°–95° C. for 1 hour to give 4'-chloro-2-biphenylylcyanamide (m.p. 106°–107° C.).

A mixture of 4'-chloro-2-biphenylylcyanamide (2.2 g) and a 33% solution of dimethylamine in ethanol (5 ml) was heated at 90°–95° C. for 2 hours to give N,N-dimethyl-N'-(4'-chloro-2-biphenylyl)guanidine (m.p. 150°–152° C.) which was recrystallised from hexane.

EXAMPLE 68

A mixture of 2-amino-4'-fluorobiphenyl (1.5 g) and benzoylisothiocyanate (1.3 g) in dichloromethane (20 ml) was heated under reflux for 6 hours to yield N-benzoyl-N'-(4'-fluoro-2-biphenylyl)thiourea as a colourless solid (m.p. 123°–124° C.).

A mixture of N-benzoyl-N'-(4'-fluoro-2-biphenylyl)-thiourea (2.8 g) and sodium hydroxide (0.4 g) and water (10 ml) was heated at 90°–95° C. for 8 hours to yield N-(4'-fluoro-2-biphenylyl)thiourea as a colourless solid (m.p. 140°–142° C.).

A mixture of N-(4'-fluoro-2-biphenylyl)thiourea (1.4 g), lead acetate trihydrate (2.15 g) and potassium hydroxide (3.18 g) in water (60 ml) was heated at 90°–95° C. for 1 hour to yield 4'-fluoro-2-biphenylylcyanamide as a colourless solid (m.p. 95°–96° C.).

A mixture of 4'-fluoro-2-biphenylylcyanamide (1 g) and 4-hydroxypiperidine (0.6 g) in ethanol (10 ml) was heated at 90°–95° C. for 3 hours to give N-(4'-fluoro-2-biphenylyl)-4-hydroxypiperidine-1-carboxamidine as a colourless solid (m.p. 132°–133° C.) which was recrystallised from ethylacetate.

EXAMPLE 69

Reaction of 2-amino-2'-fluorobiphenyl (5 g) with benzoylisothiocyanate (4.4 g) in dichloromethane (120 ml) at ambient temperature for 8 hours gave N-benzoyl-N'-(2'-fluoro-2-biphenylyl)thiourea (m.p. 110°–111° C.).

A mixture of N-benzoyl-N'-(2'-fluoro-2-biphenylyl)-thiourea (9.5 g), sodium hydroxide (1.14 g) and water (80 ml) was heated at 90°–95° C. for 8 hours to give N-(2'-fluoro-2-biphenylyl)thiourea as a colourless solid (m.p. 175°–177° C.).

A mixture of N-(2'-fluoro-2-biphenylyl)thiourea (6 g), lead acetate trihydrate (9.25 g), potassium hydroxide (13.65 g) and water (180 ml) was heated at 90°–95° C. for 3 hours to give 2'-fluoro-2-biphenylylcyanamide as a colourless solid (m.p. 68°–69° C.).

A mixture of 2'-fluoro-2-biphenylylcyanamide (2.1 g) and N-methylpiperazine (1.5 g) in ethanol (25 ml) was heated at 90°–95° C. for 3 hours to yield the free base which was reacted with fumaric acid (1.78 g) in methanol (70 ml) to give N-(2'-fluoro-2-biphenylyl)-4-methylpiperazine-1-carboxamidine difumarate (m.p. 201°–202° C.) which was recrystallised from a 2:3 mixture of methanol and ether.

EXAMPLE 70

A mixture of 2'-fluoro-2-biphenylylcyanamide (2.5 g) and 4-hydroxypiperidine (1.4 g) in ethanol (30 ml) was heated at reflux on a steam bath for 2 hours gave a yellow foamy solid which was reacted with fumaric acid (1.3 g) in methanol (10 ml) to give N-(2'-fluoro-2-biphenylyl)-4-hydroxypiperidine-1-carboxamidine fumarate as a colourless solid (m.p. 214°–215° C.) which was recrystallised from a 1:2 mixture of methanol and ether.

EXAMPLE 71

Reaction of 2-amino-3'-fluorobiphenyl (10 g) and thiophosgene (9.2 g) in a mixture of dioxane (15 ml) and water (70 ml) at ambient temperature for 1.5 hours yielded 3'-fluoro-2-biphenylylisothiocyanate as a brown oil.

Reaction of 3'-fluoro-2-biphenylylisothiocyanate (11.2 g) with ethanol (50 ml) with 28% aqueous ammonia solution (100 ml) for 24 hours at ambient temperature yielded N-(3'-fluoro-2-biphenylyl)thiourea (m.p. 157°–159° C.).

A suspension of N-(3'-fluoro-2-biphenyl)thiourea (10 g) in water (50 ml) was reacted with a solution potassium hydroxide (22.8 g) in water (50 ml) and a solution of lead acetate trihydrate (15.4 ml) in water (50 ml). The reaction mixture heated at 90°–95° C. for 1 hour to give 3'-fluoro-2-biphenylylcyanamide.

A mixture of 3'-fluoro-2-biphenylylcyanamide (4.1 g) and 4-hydroxypiperidine (1.95 g) in 1,2-dimethoxyethane (30 ml) was heated at 90°–95° C. for 4 hours to give N-(3'-fluoro-2-biphenylyl)-4-hydroxypiperidine-1-carboxamidine as a colourless solid (m.p. 147°–148° C.) which was recrystallised from ethylacetate.

EXAMPLE 72

A mixture of 3'-fluoro-2-biphenylylcyanamide (4.1 g) and N-methylpiperazine (1.9 g) in 1,2-dimethoxyethane (30 ml) was heated at 90°–95° C. for 4 hours to yield N-(3'-fluoro-2-biphenylyl)-4-methylpiperazine-1-carboxamidine (m.p. 117°–118° C.) which was recrystallised from hexane.

EXAMPLE 73

A mixture of 2-biphenylylcyanamide (4 g), 3-hydroxypiperidine (2.5 g) and ethanol (30 ml) was heated at 90°–95° C. for 8 hours to give a brown solid which was purified by chromatography on an aluminia column eluted successively with hexane, 1:4, 2:3, 3:2 and 4:1 mixtures of dichloromethane and hexane and then a 99:1 mixture of dichloromethane and methanol to yield a solid which was recrystallised from ethyl acetate to give N-(2-biphenylyl)-3-hydroxypiperidine-1-carboxamidine (m.p. 144°–145° C.).

EXAMPLE 74

A mixture of 2-biphenylylcyanamide (3.9 g), 4-piperidone oxime (4.5 g) and ethanol (50 ml) was stirred at ambient temperature for 6 hours and then at 50°–60° C. for 5 hours to give a brown solid which was purified by chromatography on an aluminia column eluted successively with hexane, 1:4, 2:3, 3:2 and 4:1 mixtures of dichloromethane and hexane and the 99:1 mixture of dichloromethane and methanol to yield a solid which was recrystallised from ethyl acetate to give N-(2-biphenylyl)-4-hydroxyiminopiperidine-1-carboxamidine (m.p. 175°–176° C.).

EXAMPLE 75

A mixture of the product of Example 49 (4 g), sodium metaperiodate (3.17 g), water (10 ml) and methanol (100 ml) was stirred at ambient temperature for 20 hours to give N-(2-biphenylyl)thiomorpholine-1-oxide-4-carboxamidine (m.p. 170°–171° C.) which was recrystallised from a 1:1 mixture of 1,2-dimethoxyethane and hexane.

EXAMPLE 76

A mixture of 4'-hydroxy-2-nitrobiphenyl (10.4 g), dimethyl sulphate (9.15 g) in acetone (350 ml) and anhydrous potassium carbonate (22 g) was heated at reflux for 10 hours to get an oil which was purified by column chromatography on silica gel (150 g, 100-200 mesh) eluted with hexane to give 4'-methoxy-2-nitrobiphenyl (m.p. 55°-56° C.).

Reduction of 4'-methoxy-2-nitrobiphenyl (9.5 g) in ethylacetate (250 ml) with stannous chloride dihydrate (47 g) at room temperature for 16 hours gave 2-amino-4'-methoxybiphenyl (m.p. 30° C.).

Reaction of 2-amino-4'-methoxybiphenyl (10 g) with thiophosgene (8.7 g) in dioxane (25 ml) and water (80 ml) at 0° C. for 3 hours gave 4'-methoxy-2-biphenylylisothiocyanate as a pale yellow oil.

Reaction of 4'-methoxy-2-biphenylylisothiocyanate (12.7 g) in ethanol (30 ml) with 28% aqueous ammonia (20 ml) at 0° C. for 2 hours gave N-(4'-methoxy-2-biphenylyl)thiourea (m.p. 158°-159° C.).

Reaction of N-(4'-methoxy-2-biphenylyl)thiourea (14.7 g) with methyliodide (9.3 g) in methanol (60 ml) at gentle reflux on a hot water bath for 3 hours gave 1-(4'-methoxy-2-biphenylyl)-2-methyl-2-thiopseudourea hydroiodide as a semisolid. Reaction of the above hydroiodide (8 g) in dichloromethane (100 ml) with 10% aqueous sodium hydroxide solution (25 ml) at 0° C. gave 1-(4'-methoxy-2-biphenylyl)-2-methyl-2-thiopseudourea as a pale yellow solid (m.p. 94°-96° C.).

A mixture of 1-(4'-methoxy-2-biphenylyl)-2-methyl-2-thiopseudourea (5.6 g) in absolute ethanol (40 ml) and a 33% solution of dimethylamine in ethanol (25 ml) was stored at room temperature for 3 months to give 30 N-(4'-methoxy-2-biphenylyl)-N',N'-dimethyl-guanidine (m.p. 130°-131° C.) which was recrystallised from ethyl-acetate.

A sample (1.5 g) was reacted with fumaric acid (0.6 g) in methanol (10 ml) to give N-(4'-methoxy-2-biphenylyl-N',N'-dimethylguanidine fumarate (m.p. 190°-191° C.) which was recrystallised from a 1:3 mixture of methanol and ether.

EXAMPLE 77

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

| | Parts by weight |
|---|---|
| Active compound | 10 |
| Lactose | 190 |
| Maize starch | 22 |
| Polyvinylpyrrolidone | 10 |

-continued

| | Parts by weight |
|---|---|
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

I claim:

1. A compound of formula I

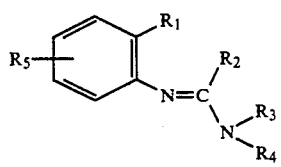

and pharmaceutically acceptable salts thereof, in which
$R_1$ is phenyl optionally substituted by halo, alkyl of 1 to 3 carbon atoms, alkoxy of 1 to 3 carbon atoms, alkanoyl of 2 to 4 carbon atoms, or a group of formula $S(O)_n R_8$ in which $n=0$ or 1 and $R_8$ is an alkyl group of 1 to 3 carbon atoms;
$R_2$ is a group of formula II

in which $R_6$ and $R_7$, which are the same or different, are H or an alkyl group containing 1 to 4 carbon atoms; $R_3$ is H or a straight or branched aliphatic group of 1 to 4 carbon atoms;

$R_4$ is (a) H, (b) a straight or branched aliphatic group of 1 to 6 carbon atoms optionally substituted by hydroxy or an acylated derivative thereof, by an alkoxy group containing 1 to 3 carbon atoms, by an alkylthio group containing 1 to 3 carbon atoms, by an optionally alkylated amino group, by a carbocyclic group containing 3 to 7 carbon atoms, by pyridyl or by cyano, (c) a carbocyclic ring containing 3 to 7 carbon atoms and optionally substituted by hydroxy with the proviso that $R_3$, $R_4$, $R_6$ and $R_7$ are not all methyl when $R_1$ is phenyl; or the group $R_2$ and the group $R_3$ together with the carbon and nitrogen atoms to which they are attached form a heterocyclic ring of formula IV

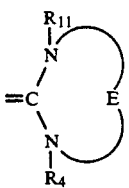

in which $R_4$ is an hereinbefore described except that $R_4$ cannot be H, in which $R_{11}$ is H or an alkyl group containing 1 or 2 carbon atoms, and E is an alkylene group of 2 to 4 carbon atoms optionally substituted by one or more alkyl groups containing 1 to 3 carbon atoms; or $R_3$ and $R_4$ together with the nitrogen atom to which they are attached form a heterocyclic ring of formula V

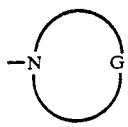

in which

G is an alkylene group of 4 to 6 carbon atoms optionally interrupted by oxygen, sulphur, sulphinyl, sulphonyl, or nitrogen optionally substituted by (a) a carbocyclic ring containing 3 to 7 carbon atoms (b) a methylsulphonyl group or (c) an alkyl group containing 1 to 3 carbon atoms and optionally substituted by hydroxy or an alkoxy group containing 1 to 3 carbon atoms, said alkylene group being optionally substituted by (a) one or more alkyl groups containing 1 to 3 carbon atoms and optionally substituted by hydroxy, (b) by one or more hydroxy groups or an ester thereof, (c) by one or more alkoxy groups, (d) by oxo or oxime or oxime ether or (e) by one or more groups of formula $S(O)_m R_8$ in which $m=0$ or 1 and $R_8$ is an alkyl group containing 1 to 3 carbon atoms and $R_5$ represents H or one or more optional substituents selected from halo, alkyl groups containing 1 to 4 carbon atoms, alkoxy groups containing 1 to 3 carbon atoms, trifluoromethyl, or groups of formula $S(O)_m R_8$ in which m is 0,1 or 2 and $R_8$ is an alkyl group containing 1 to 3 carbon atoms.

2. A compound of formula I as claimed in claim 1 in which $R_1$ is phenyl, 2-fluorophenyl, 3-fluorophenyl, 4-fluorophenyl, 4-chlorophenyl, 4-methoxyphenyl, 3-methylphenyl, 4-methylphenyl, 3-methylthiophenyl, 3-methanesulphonylphenyl, 4-methanesulphonylphenyl or 4-acetylphenyl.

3. A compound of formula I as claimed in claim 1 in which $R_2$ is a group of formula II in which $R_6$ and $R_7$ are independently H or methyl.

4. A compound of formula I as claimed in claim 1 in which $R_3$ is H or an alkyl group containing 1 to 3 carbon atoms and in which $R_4$ is (a) H, (b) an alkyl group of 1 to 3 carbon atoms optionally substituted by methoxy, pyridyl or dimethylamino or (c) a phenyl group substituted by hydroxy.

5. A compound of formula I as claimed in claim 1 in which E is $-(CH_2)_2-$, $R_{11}$ is H or methyl and $R_4$ is methyl, n-butyl or 2-hydroxyethyl.

6. A compound of formula I as claimed in claim 5 in which formula IV represents 1-methyl-2-imidazolidinylidene, 1-(n-butyl)-2-imidazolidinylidene, 1-(2-ethyl)-2-imidazolindinylidene or 1,3-dimethyl-2-imidazolidinylidene.

7. A compound of formula I as claimed in claim 1 in which G represents a group selected from
—$(CH_2)_4$—,
—$(CH_2)_5$—,
—$CH_2CH=CH-(CH_2)_2$—,
—$(CH_2)_2O(CH_2)_2$—,
—$(CH_2)_2OCHMeCH_2$—
—$CMe_2CH_2O(CH_2)_2$—
—$(CH_2)_2S(CH_2)_2$—,
—$(CH_2)_2SO(CH_2)_2$—,
—$(CH_2)_2SO_2(CH_2)_2$—,
—$(CH_2)_2NMe(CH_2)_2$—,
—$(CH_2)_2NEt(CH_2)_2$—
—$(CH_2)_2N(SO_2Me)(CH_2)_2$—,
—$(CH_2)_2N(CH_2CH_2OH)(CH_2)_2$—,
—$(CH_2)_2CHMe(CH_2)_2$—,
—$CH_2CH(OH)(CH_2)_2$—,
—$CH_2CH(OH)(CH_2)_3$—,
—$CH_2CH(CH_2OH)(CH_2)_3$—,
—$(CH_2)_2CH(CH_2OH)(CH_2)_2$—,
—$(CH_2)_2(OH)(CH_2)_2$—,
—$(CH_2)_2C(OH)(Me)(CH_2)_2$—,
—$(CH_2)_2(OMe)(CH_2)_2$—,
—$CH_2CH(OMe)(CH_2)_3$—,
—$(CH_2)_2CH(CONMe_2)(CH_2)_2$—
—$(CH_2)_2CO(CH_2)_2$—
—$(CH_2)_2C=NOH(CH_2)_2$—,
—$(CH_2)_2C=NOMe(CH_2)_2$—.

8. A compound of formula I as claimed in claim 1 in which the group —$NR_3R_4$ is 3-hydroxy-1-pyrrolidinyl, piperidino, 1,2,5,6-tetrahydropyridyl, 4-methylpiperidino, 3-hydroxypiperidino, 4-hydroxypiperidino, 4-hydroxy-4-methylpiperidino, 3-methoxypiperidino, 4-methoxypiperidino, 3-hydroxymethylpiperidino, 4-hydroxymethylpiperidino, 4-dimethylcarbamoylpiperidino, 4-piperidinon-1-yl, 4-piperidinon-1-yl oxime, 4-piperidinon-1-yl, oxime-O-methyl ether, morpholino, 2-methylmorpholino, 3,3-dimethylmorpholino, thiomorpholino, thiomorpholino-1-oxide, thiomorpholino-1,1-dioxide, 4-methyl-1-piperazinyl, 4-ethyl-1-piperazinyl, 4-(2-hydroxyethyl)-1-piperazinyl, 4-methylsulphonyl-1-piperazinyl.

9. A compound of formula I as claimed in claim 1 in which the group —$N=C(R_2)NR_3R_4$ is
N,N-dimethylguanidino,
N,N'-dimethylguanidino,
N-methyl-N-(2-pyridylethyl)guanidino,
N-ethyl-N-(2-methoxyethyl)guanidino,
N-methyl-N-(2-dimethylaminoethyl)guanidino,
N-(4-hydroxyphenyl)-N-methylguanidino,
N,N-(3-oxapentamethylene)guanidino,
N,N-(2-methyl-3-oxapentamethylene)guanidino,
N,N-(1,1-dimethyl-3-oxapentamethylene)guanidino,
N,N-(3-thiapentamethylene)guanidino,
N,N-(3-thiopentamethylene)guanidino S-oxide,
N,N-(3-thiopentamethylene)guanidino S-dioxide,
N,N-(3-methyl-3-azapentamethylene)guanidino,
N,N-(3-ethyl-3-azapentamethylene)guanidino,
N,N-[3-(2-hydroxyethyl)-3-azapentamethylene]guanidino, N,N-(3-methylsulphonyl-3-azapentamethylene)-guanidino,
N,N-(2-hydroxytetramethylene)guanidino,
N,N-pentamethyleneguanidino,
N,N-(2-pentenylene)guanidino,
N,N-(3-methylpentamethylene)guanidino,
N,N-(2-hydroxypentamethylene)guanidino,
N,N-(3-hydroxypentamethylene)guanidino,
N,N-(3-hydroxy-3-methylpentamethylene)guanidino,
N,N-(2-hydroxymethylpentamethylene)guanidino,
N,N-(3-hydroxymethylpentamethylene)guanidino,
N,N-(3-dimethylcarbamoylpentamethylene)guanidino,
N,N-(2-methoxypentamethylene)guanidino,
N,N-(3-methoxypentamethylene)guanidino,
N,N-(3-oxopentamethylene)guanidino,
N,N-(3-hydroxyiminopentamethylene)guanidino,
N,N-(3-methoxyiminopentamethylene)guanidino.

10. A compound of formula I as claimed in claim 1 in which $R_5$ represents one or more substituents selected from fluoro, methyl, methoxy or methythio.

11. A compound as claimed in claim 1 selected from:
N-(2-biphenylyl)-4-hydroxypiperidine-1-carboxamidine
N-(4'-fluoro-2-biphenylyl)-4-hydroxypiperidine-1-carboxamidine
N-(5-fluoro-2-biphenylyl(4-hydroxypiperidine-1-carboxamidine.

12. A pharmaceutical composition comprising a pharmaceutically acceptable diluent or carrier and a hypoglycaemically effective amount of a compound of formula I

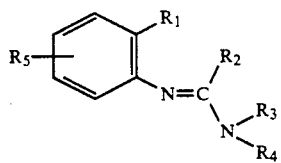

and pharmaceutically acceptable salts thereof, in which
$R_1$ is phenyl optionally substituted by halo, alkyl of 1 to 3 carbon atoms, alkoxy of 1 to 3 carbon atoms, alkanoyl of 2 to 4 carbon atoms, or a group of formula $S(O)_nR_8$ in which n=0 or 1 and $R_8$ is an alkyl group of 1 to 3 carbon atoms;
$R_2$ is a group of formula II

in which
$R_6$ and $R_7$, which are the same or different, are H or an alkyl group containing 1 to 4 carbon atoms; $R_1$ is H or a straight or branched aliphatic group of 1 to 4 carbon atoms;
$R_4$ is (a) H, (b) a straight or branched aliphatic group of 1 to 6 carbon atoms optionally substituted by hydroxy or an acylated derivative thereof, by an alkoxy group containing 1 to 3 carbon atoms, by an alkylthio group containing 1 to 3 carbon atoms, by an optionally alkylated amino group, by a carbocyclic group containing 3 to 7 carbon atoms, by pyridinyl or by cyano, (c) a carbocyclic ring containing 3 to 7 carbon atoms and optionally substituted by hydroxy with the proviso that $R_3$, $R_4$, $R_6$ and $R_7$ are not all methyl when $R_1$ is phenyl; or
the group $R_2$ and the group $R_3$ together with the carbon and nitrogen atoms to which they are attached form a heterocyclic ring of formula IV

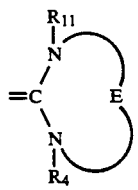

in which $R_4$ is as hereinbefore described except that $R_4$ cannot be H, in which $R_{11}$ is H or an alkyl group containing 1 or 2 carbon atoms, and E is an alkylene group of 2 to 4 carbon atoms optionally substituted by one or more alkyl groups containing 1 to 3 carbon atoms; or $R_3$ and $R_4$ together with the nitrogen atom to which they are attached form a heterocyclic ring of formula V

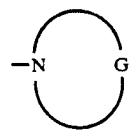

in which G is an alkylene group of 4 to 6 carbon atoms optionally interrupted by oxygen, sulphur, sulphinyl, sulphonyl, or nitrogen optionally substituted by (a) a carbocyclic ring containing 3 to 7 carbon atoms (b) a methylsulphonyl group or (c) an alkyl group containing 1 to 3 carbon atoms and optionally substituted by hydroxy or an alkoxy group containing 1 to 3 carbon atoms, said alkylene group being optionally substituted by (a) one or more alkyl groups containing 1 to 3 carbon atoms and optionally substituted by hydroxy, (b) by one or more hydroxy groups or an ester thereof, (c) by one or more alkoxy groups, (d) by oxo or oxime or oxime ether or (e) by one or more groups of formula $S(O)_mR_8$ in which m=0 or 1 and $R_8$ is an alkyl group containing 1 to 3 carbon atoms and
$R_5$ represents H or one or more optional substituents selected from halo, alkyl groups containing 1 to 4 carbon atoms, alkoxy groups containing 1 to 3 carbon atoms, trifluoromethyl, or groups of formula $S(O)_mR_8$ in which m is 0.1 or 2 and $R_8$ is an alkyl group containing 1 to 3 carbon atoms.

13. A pharmaceutical composition as claimed in claim 12 in which $R_1$ is phenyl, 2-fluorophenyl, 3-fluorophenyl, 4-fluorophenyl, 4-chlorophenyl, 4-methoxyphenyl, 3-methylphenyl, 4-methylphenyl, 3-methylthiophenyl, 3-methanesulphonylphenyl, 4-methanesulphonylphenyl or 4-acetylphenyl.

14. A pharmaceutical composition as claimed in claim 12 in which a group of formula II in which $R_6$ and $R_7$ are independently H or methyl.

15. A pharmaceutical composition as claimed in claim 12 in which $R_3$ is H or an alkyl group containing 1 to 3 carbon atoms and in which $R_4$ is (a) H, (b) an alkyl group of 1 to 3 carbon atoms optionally substituted by methoxy, pyridyl or dimethylamino or (c) a phenyl group substituted by hydroxy.

16. A pharmaceutical composition as claimed in claim 12 in which E is —(CH$_2$)$_2$—, R$_{11}$ is H or methyl and R$_4$ is methyl, n-butyl or 2-hydroxyethyl.

17. A pharmaceutical composition as claimed in claim 16 in which formula IV represents 1-methyl-2-imidazolidinylene, 1-(n-butyl)-2-imidazolidinylidene, 1-(2-hydroxyethyl)-2-imidazolidinylidene or 1,3-dimethyl-2-imidazolidinylidene.

18. A pharmaceutical composition as claimed in claim 12 in which G represents a group selected from
—(CH$_2$)$_4$—,
—(CH$_2$)$_5$—,
—CH$_2$CH=CH—(CH$_2$)$_2$—,
—(CH$_2$)$_2$O(CH$_2$)$_2$—,
—(CH$_2$)$_2$OCHMeCH$_2$—
—CMe$_2$CH$_2$O(CH$_2$)$_2$—
—(CH$_2$)$_2$S(CH$_2$)$_2$—,
—(CH$_2$)$_2$SO(CH$_2$)$_2$—,
—(CH$_2$)$_2$SO$_2$(CH$_2$)$_2$—,
—(CH$_2$)$_2$NMe(CH$_2$)$_2$—,
—(CH$_2$)$_2$NEt(CH$_2$)$_2$—
—(CH$_2$)$_2$N(SO$_2$Me)(CH$_2$)$_2$—,
—(CH$_2$)$_2$N(CH$_2$CH$_2$OH)(CH$_2$)$_2$—,
—(CH$_2$)$_2$CHMe(CH$_2$)$_2$—,
—CH$_2$CH(OH)(CH$_2$)$_2$—,
—CH$_2$CH(OH)(CH$_2$)$_3$—,
—CH$_2$CH(CH$_2$OH)(CH$_2$)$_3$—,
—(CH$_2$)$_2$CH(CH$_2$OH)(CH$_2$)$_2$—,
—(CH$_2$)$_2$(OH)(CH$_2$)$_2$—,
—(CH$_2$)$_2$C(OH)(Me)(CH$_2$)$_2$—,
—(CH$_2$)$_2$(OMe)(CH$_2$)$_2$—,
—CH$_2$CH(OMe)(CH$_2$)$_3$—,
—(CH$_2$)$_2$CH(CONMe$_2$)(CH$_2$)$_2$—
—(CH$_2$)$_2$CO(CH$_2$)$_2$—
—(CH$_2$)$_2$C=NOH(CH$_2$)$_2$—,
—(CH$_2$)$_2$C=NOMe(CH$_2$)$_2$—.

19. A pharmaceutical composition as claimed in claim 12 in which the group —NR$_3$R$_4$ is 3-hydroxy-1-pyrrolidinyl, piperidino, 1,2,5,6-tetrahydropyridyl, 4-methylpiperidino, 3-hydroxypiperidino, 4-hydroxypiperidino, 4-hydroxy-4-methylpiperidino, 3-methoxypiperidino, 4-methoxypiperidino, 3-hydroxymethylpiperidino, 4-hydroxymethylpiperidino, 4-dimethylcarbamoylpiperidino, 4-piperidinon-1-yl, 4-piperidinon-1-yl oxime, 4-piperidinon-1-yl oxime-O-methyl ether, morpholino, 2-methylmorpholino, 3,3-dimethylmorpholino, thiomorpholino, thiomorpholino-1-oxide, thiomorpholino-1,1-dioxide, 4-methyl-1-piperazinyl, 4-ethyl-1-piperazinyl, 4-(2-hydroxyethyl)-1-piperazinyl, 4-methylsulphonyl-1-piperazinyl.

20. A pharmaceutical composition as claimed in claim 12 in which the group —N=C(R$_2$)NR$_3$R$_4$ is
N-methylpivalamidino,
cyclohexanecarboxamidino,
N,N-dimethylguanidino,
N,N'-dimethylguanidino,
N-methyl-N-(2-pyridylethyl)guanidino,
N-ethyl-N-(2-methoxyethyl)guanidino,
N-methyl-N-(2-dimethylaminoethyl)guanidino,
N-(4-hydroxyphenyl)-N-methylguanidino,
N,N-(3-oxapentamethylene)guanidino,
N,N-(2-methyl-3-oxapentamethylene)guanidino,
N,N-(1,1-dimethyl-3-oxapentamethylene)guanidino,
N,N-(3-thiapentamethylene)guanidino,
N,N-(3-thiopentamethylene)guanidino S-oxide,
N,N-(3-thiopentamethylene)guanidino S-dioxide,
N,N-(3-methyl-3-azapentamethylene)guanidino,
N,N-(3-ethyl-3-azapentamethylene)guanidino,
N,N-[3-(2-hydroxyethyl)-3-azapentamethylene]-guanidino,
N,N-(3-methylsulphonyl-3-azapentamethylene)-guanidino,
N,N-(2-hydroxytetramethylene)guanidino,
N,N-pentamethyleneguanidino,
N,N-(2-pentenylene)guanidino,
N,N-(3-methylpentamethylene)guanidino,
N,N-(2-hydroxypentamethylene)guanidino,
N,N-(3-hydroxypentamethylene)guanidino,
N,N-(3-hydroxy-3-methylpentamethylene)guanidino,
N,N-(2-hydroxymethylpentamethylene)guanidino,
N,N-(3-hydroxymethylpentamethylene)guanidino,
N,N-(3-dimethylcarbamoylpentamethylene)guanidino,
N,N-(2-methoxypentamethylene)guanidino,
N,N-(3-methoxypentamethylene)guanidino,
N,N-(3-oxopentamethylene)guanidino
N,N-(3-hydroxyiminopentamethylene)guanidino
N,N-(3-methoxyiminopentamethylene)guanidino.

21. A pharmaceutical composition as claimed in claim 12 in which R$_5$ represents one or more substituents selected from fluoro, methyl, methoxy or methylthio.

22. A pharmaceutical composition as claimed in claim 12 wherein the compound of formula I is selected from:
N-(2-biphenylyl)-4-hydroxypiperidine-1-carboxamidine
N-(4'-fluoro-2-biphenylyl)-4-hydroxypiperidine-1-carboxamidine
N-(5-fluoro-2-biphenylyl(4-hydroxypiperidine-1-carboxamidine.

23. A method of treating hyperglycaemia comprising administering to a subject in need thereof a hypoglycaemically effective amount of a compound of formula I

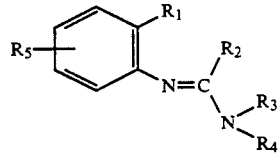

and pharmaceutically acceptable salts thereof, in which
R$_1$ is phenyl optionally substituted by halo, alkyl of 1 to 3 carbon atoms, alkoxy of 1 to 3 carbon atoms, alkanoyl of 2 to 4 carbon atoms, or a group of formula S(O)$_n$R$_8$ in which n=0 or 1 and R$_8$ is an alkyl group of 1 to 3 carbon atoms;
R$_2$ is a group of formula II

in which
R$_6$ and R$_7$, which are the same or different, are H or an alkyl group containing 1 to 4 carbon atoms; R$_3$ is H or a straight or branched aliphatic group of 1 to 4 carbon atoms;
R$_4$ is (a) H, (b) a straight or branched aliphatic group of 1 to 6 carbon atoms optionally substituted by hydroxy or an acylated derivative thereof, by an alkoxy group containing 1 to 3 carbon atoms, by an alkylthio group containing 1 to 3 carbon atoms, by an optionally alkylated amino group, by a carbocyclic group containing 3 to 7 carbon atoms, by pyridyl or by cyano, (c) a carbocyclic ring containing 3 to 7 carbon atoms and optionally substituted by hydroxy with the proviso that $R_3$, $R_4$, $R_6$ and $R_7$ are not all methyl when $R_1$ is phenyl; or the group $R_2$ and the group $R_3$ together with the carbon and nitrogen atoms to which they are attached from a heterocyclic ring of formula IV

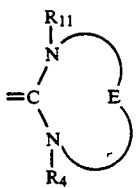

in which $R_4$ is as hereinbefore described except that $R_4$ cannot be H, in which $R_{11}$ is H or an alkyl group containing 1 or 2 carbon atoms, and E is an alkylene group of 2 to 4 carbon atoms optionally substituted by one or more alkyl groups containing 1 to 3 carbon atoms; or $R_3$ and $R_4$ together with the nitrogen atom to which they are attached form a heterocyclic ring of formula V

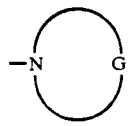

in which

G is an alkylene group of 4 to 6 carbon atoms optionally interrupted by oxygen, sulphur, sulphinyl, sulphonyl, or nitrogen optionally substituted by (a) a carbocyclic ring containing 3 to 7 carbon atoms (b) a methylsulphonyl group or (c) an alkyl group containing 1 to 3 carbon atoms and optionally substituted by hydroxy or an alkoxy group containing 1 to 3 carbon atoms, said alkylene group being optionally substituted by (a) one or more alkyl groups containing 1 to 3 carbon atoms and optionally substituted by hydroxy, (b) by one or more hydroxy groups or an ester thereof, (c) by one or more alkoxy groups, (d) by oxo or oxime or oxime ether or (e) by one or more groups of formula $S(O)_m R_8$ in which m=0 or 1 and $R_8$ is an alkyl group containing 1 to 3 carbon atoms and $R_5$ represents H or one or more optional substituents selected from halo, alkyl groups containing 1 to 4 carbon atoms, alkoxy groups containing 1 to 3 carbon atoms, trifluoromethyl, or groups of formula $S(O)_m R_8$ in which m is 0.1 or 2 and $R_8$ is an alkyl group containing 1 to 3 carbon atoms.

24. A method as claimed in claim 23 in which $R_1$ is phenyl, 2-fluorophenyl, 3-fluorophenyl, 4-fluorophenyl, 4-chlorophenyl, 4-methoxyphenyl, 3-methylphenyl, 4-methylphenyl, 3-methylthiophenyl, 3-methanesulphonyl-phenyl, 4-methanesulphonylphenyl or 4-acetylphenyl.

25. A method as claimed in claim 23 in which $R_2$ is a group of formula II in which $R_6$ and $R_7$ are independently H or methyl.

26. A method as claimed in claim 23 in which $R_3$ is H or an alkyl group containing 1 to 3 carbon atoms and in which $R_4$ is (a) H, (b) an alkyl group of 1 to 3 carbon atoms optionally substituted by methoxy, pyridyl or dimethylamino or (c) a phenyl group substituted by hydroxy.

27. A method as claimed in claim 23 in which E is —$(CH_2)_2$—, $R_{11}$ is H or methyl and $R_4$ is methyl, n-butyl or 2-hydroxyethyl.

28. A method as claimed in claim 27 in which formula IV represents 1-methyl-2-imidazolidinylidene, 1-(n-butyl)-2-imidazolidinylidene, 1-(2-hydroxyethyl)-2-imidazolidinylidene or 1,3-dimethyl-2-imidazolidinylidene.

29. A method as claimed in claim 23 in which G represents a group selected from
—$(CH_2)_4$—,
—$(CH_2)_5$—,
—$CH_2CH=CH—(CH_2)_2$—,
—$(CH_2)_2O(CH_2)_2$—,
—$(CH_2)_2OCHMeCH_2$—
—$CMe_2CH_2O(CH_2)_2$—
—$(CH_2)_2S(CH_2)_2$—,
—$(CH_2)_2SO(CH_2)_2$—,
—$(CH_2)_2SO_2(CH_2)_2$—,
—$(CH_2)_2NMe(CH_2)_2$—,
—$(CH_2)_2NEt(CH_2)_2$—
—$(CH_2)_2N(SO_2Me)(CH_2)_2$—,
—$(CH_2)_2N(CH_2CH_2OH)(CH_2)_2$—,
—$(CH_2)_2CHMe(CH_2)_2$—,
—$CH_2CH(OH)(CH_2)_2$—,
—$CH_2CH(OH)(CH_2)_3$—,
—$CH_2CH(CH_2OH)(CH_2)_3$—,
—$(CH_2)_2CH(CH_2OH)(CH_2)_2$—,
—$(CH_2)_2(OH)(CH_2)_2$—,
—$(CH_2)_2C(OH)(Me)(CH_2)_2$—,
—$(CH_2)_2(OMe)(CH_2)_2$—,
—$CH_2CH(OMe)(CH_2)_3$—,
—$(CH_2)_2CH(CONMe_2)(CH_2)_2$—
—$(CH_2)_2CO(CH_2)_2$—
—$(CH_2)_2C=NOH(CH_2)_2$—,
—$(CH_2)_2C=NOMe(CH_2)_2$—.

30. A method as claimed in claim 23 in which the group —$NR_3R_4$ is 3-hydroxy-1-pyrrolidinyl, piperidino, 1,2,5,6-tetrahydropyridyl, 4-methylpiperidino, 3-hydroxypiperidino, 4-hydroxypiperidino, 4-hydroxy-4-methylpiperidino, 3-methoxypiperidino, 4-methoxypiperidino, 3-hydroxymethylpiperidino, 4-hydroxymethylpiperidino, 4-dimethylcarbamoylpiperidino, 4-piperidinon-1-yl, 4-piperidinon-1-yl oxime, 4-piperidinon-1-yl oxime-O-methyl ether, morpholino, 2-methylmorpholino, 3,3-dimethylmorpholino, thiomorpholino, thiomorpholino-1-oxide, thiomorpholino-1,1-dioxide, 4-methyl-1-piperazinyl, 4-ethyl-1-piperazinyl, 4-(2-hydroxyethyl)-1-piperazinyl, 4-methyl-sulphonyl-1-piperazinyl.

31. A method as claimed in claim 23 in which the group —$N=C(R_2)NR_3R_4$ is
N,N-dimethylguanidino,
N,N'-dimethylguanidino,
N-methyl-N-(2-pyridylethyl)guanidino,
N-ethyl-N-(2-methoxyethyl)guanidino,
N-methyl-N-(2-dimethylaminoethyl)guanidino,
N-(4-hydroxyphenyl)-N-methylguanidino,
N,N-(3-oxapentamethylene)guanidino,
N,N-(2-methyl-3-oxapentamethylene)guanidino,
N,N-(1,1-dimethyl-3-oxapentamethylene)guanidino,
N,N-(3-thiapentamethylene)guanidino,
N,N-(3-thiopentamethylene)guanidino S-oxide,
N,N-(3-thiopentamethylene)guanidino S-dioxide,
N,N-(3-methyl-3-azapentamethylene)guanidino,
N,N-(3-ethyl-3-azapentamethylene)guanidino, N,N-[3-(2-hydroxyethyl)-3-azapentamethylene]-guanidino,
N,N-(3-methylsulphonyl-3-azapentamethylene)-guanidino,
N,N-(2-hydroxytetramethylene)guanidino,
N,N-pentamethyleneguanidino,
N,N-(2-pentenylene)guanidino,
N,N-(3-methylpentamethylene)guanidino,
N,N-(2-hydroxypentamethylene)guanidino,
N,N-(3-hydroxypentamethylene)guanidino,
N,N-(3-hydroxy-3-methylpentamethylene)guanidino,
N,N-(2-hydroxymethylpentamethylene)guanidino,
N,N-(3-hydroxymethylpentamethylene)guanidino,
N,N-(3-dimethylcarbamoylpentamethylene)guanidino,
N,N-(2-methoxypentamethylene)guanidino,
N,N-(3-methoxypentamethylene)guanidino,
N,N-(3-oxopentamethylene)guanidino
N,N-(3-hydroxyiminopentamethylene)guanidino
N,N-(3-methoxyiminopentamethylene)guanidino.

32. A method as claimed in claim 23 in which $R_5$ represents one or more substituents selected from fluoro, methyl, methoxy or methylthio.

33. A method as claimed in claim 23 wherein the compound of formula I is selected from:
N-(2-biphenylyl)-4-hydroxypiperidine-1-carboxamidine
N-(4'-fluoro-2-biphenylyl)-4-hydroxypiperidine-1-carboxamidine
N-(5-fluoro-2-biphenylyl(4-hydroxypiperidine-1-carboxamidine.

* * * * *

UNITED STATES PATENT AND TRADEMARK OFFICE
CERTIFICATE OF CORRECTION

PATENT NO. : 5,302,720
DATED : April 12, 1994
INVENTOR(S) : B. Gopalan

It is certified that error appears in the above-identified patent and that said Letters Patent is hereby corrected as shown below:

Column 30, line 7, for "(2-ethyl)" read "(2-hydroxyethyl)".

Column 30, line 29, for "-$(CH_2)_2(OH)(CH_2)_2$-" read "-$(CH_2)_2CH(OH)(CH_2)_2$-".

Column 30, line 31, for "-$(CH_2)_2(OMe)(CH_2)_2$-" read "-$(CH_2)_2CH(OMe)(CH_2)_2$-".

Column 30, line 45, for "4-piperidinon-1-yl," read "4-piperidinon-1-yl".

Column 30, line 63, for "3-thio" read "3-thia".

Column 30, line 64, for "3-thio" read "3-thia" and for "S-dioxide" read "S,S-dioxide".

Column 31, line 57, for "$R_1$" read "$R_3$".

Column 31, line 67, for "pyridinyl" read "pyridyl".

Column 32, line 52, for "0.1" read "0, 1".

Column 32, line 61, for "in which a group" read "in which $R_2$ is a group".

Column 33, line 29, for "-$(CH_2)_2(OH)(CH_2)_2$-" read "-$(CH_2)_2CH(OH)(CH_2)_2$-".

UNITED STATES PATENT AND TRADEMARK OFFICE
CERTIFICATE OF CORRECTION

PATENT NO. : 5,302,720
DATED : April 12, 1994
INVENTOR(S) : B. Gopalan

It is certified that error appears in the above-identified patent and that said Letters Patent is hereby corrected as shown below:

Column 33, line 31, for "-(CH$_2$)$_2$(OMe)(CH$_2$)$_2$-" read "-(CH$_2$)$_2$CH(OMe)(CH$_2$)$_2$-".

Column 33, line 65, for "3-thio" read "3-thia".

Column 33, line 66, for "3-thio" read "3-thia" and for "S-dioxide" read "S,S-dioxide".

Column 35, line 54, for "0.1" read "0, 1".

Column 36, line 31, for "-(CH$_2$)$_2$(OH)(CH$_2$)$_2$-" read "-(CH$_2$)$_2$CH(OH)(CH$_2$)$_2$-".

Column 36, line 33, for "-(CH$_2$)$_2$(OMe)(CH$_2$)$_2$-" read "-(CH$_2$)$_2$CH(OMe)(CH$_2$)$_2$-".

Column 36, line 65, for "3-thio" read "3-thia".

Column 36, line 66, for "3-thio" read "3-thia" and for "S-dioxide" read "S,S-dioxide".

Signed and Sealed this

Twentieth Day of September, 1994

BRUCE LEHMAN

Attest:

Attesting Officer

Commissioner of Patents and Trademarks